US 11,752,258 B2

(12) United States Patent
Damestani et al.

(10) Patent No.: US 11,752,258 B2
(45) Date of Patent: Sep. 12, 2023

(54) DRUG DELIVERY DEVICE WITH STERILE FLUID FLOWPATH AND RELATED METHOD OF ASSEMBLY

(71) Applicant: AMGEN INC., Thousand Oaks, CA (US)

(72) Inventors: Yasaman Damestani, Thousand Oaks, CA (US); Lawrence S. Ring, Laguna Beach, CA (US)

(73) Assignee: AMGEN INC., Thousand Oaks, CA (US)

( * ) Notice: Subject to any disclaimer, the term of this patent is extended or adjusted under 35 U.S.C. 154(b) by 1013 days.

(21) Appl. No.: 16/485,407

(22) PCT Filed: Jan. 17, 2018

(86) PCT No.: PCT/US2018/014014
§ 371 (c)(1),
(2) Date: Aug. 12, 2019

(87) PCT Pub. No.: WO2018/151890
PCT Pub. Date: Aug. 23, 2018

(65) Prior Publication Data
US 2019/0374707 A1 Dec. 12, 2019

Related U.S. Application Data

(60) Provisional application No. 62/460,559, filed on Feb. 17, 2017.

(51) Int. Cl.
*A61M 5/145* (2006.01)
*A61J 1/20* (2006.01)
(Continued)

(52) U.S. Cl.
CPC .......... *A61M 5/1456* (2013.01); *A61J 1/2024* (2015.05); *A61M 5/24* (2013.01); *A61J 1/1406* (2013.01); *A61M 5/285* (2013.01)

(58) Field of Classification Search
CPC ...... A61M 5/1456; A61M 5/24; A61M 5/285; A61M 5/14248; A61M 2005/14252;
(Continued)

(56) References Cited

U.S. PATENT DOCUMENTS 5,330,426 A * 7/1994 Kriesel ............... A61M 5/2429
604/82
5,827,262 A 10/1998 Neftel et al.
(Continued)

FOREIGN PATENT DOCUMENTS

EP 1495775 A1 1/2005
JP H09502116 A 3/1997
(Continued)

OTHER PUBLICATIONS

European Patent Application No. 18703137.2, Communication Pursuant to Article 94(3) EPC, dated May 12, 2021.
(Continued)

*Primary Examiner* — Jason E Flick
(74) *Attorney, Agent, or Firm* — MARSHALL, GERSTEIN & BORUN LLP

(57) ABSTRACT

Drug delivery devices and related methods of assembly are disclosed. The drug delivery device may include a housing and a container disposed therein. The container may include a reservoir containing a drug and a movable stopper. A first seal member may be connected to the container at a distal end of the reservoir. A first removable membrane may cover an exterior surface of the first seal member to maintain sterility of that surface prior to operation of the device. A fluid pathway assembly may be configured to establish fluid communication with the reservoir during operation of the device. A second seal member may be connected to a first end of the fluid pathway assembly. A second removable membrane may cover an exterior surface of the second seal
(Continued)

member to maintain sterility of that surface prior to operation of the device.

21 Claims, 9 Drawing Sheets

(51) Int. Cl.
    *A61M 5/24*     (2006.01)
    *A61J 1/14*     (2023.01)
    *A61M 5/28*     (2006.01)

(58) Field of Classification Search
    CPC ........ A61M 5/14; A61M 5/142; A61M 5/145; A61M 5/1452; A61M 5/288; A61M 5/14244; A61J 1/2024; A61J 1/1406
    See application file for complete search history.

(56) References Cited

U.S. PATENT DOCUMENTS

| | | |
|---|---|---|
| 6,022,339 A | 2/2000 | Fowles et al. |
| 2006/0200073 A1 | 9/2006 | Radmer et al. |
| 2014/0008366 A1 | 1/2014 | Genosar |
| 2014/0025014 A1 | 1/2014 | Radmer et al. |
| 2015/0273161 A1 | 10/2015 | Bengtsson et al. |

FOREIGN PATENT DOCUMENTS

| | | |
|---|---|---|
| JP | 2014503298 A | 2/2014 |
| JP | 2014528791 A | 10/2014 |
| JP | 2016523123 A | 8/2016 |
| JP | 2016525428 A | 8/2016 |
| JP | 2016528017 A | 9/2016 |
| WO | WO-2013040032 A1 | 3/2013 |
| WO | WO-2014194183 A2 | 12/2014 |
| WO | WO-2015015379 A1 | 2/2015 |
| WO | WO-2015027174 A1 | 2/2015 |
| WO | WO-2016/133947 A1 | 8/2016 |
| WO | WO-2016141082 A1 | 9/2016 |

OTHER PUBLICATIONS

Japanese Patent Application No. 2019-542484, Notice of Rejection, dated Sep. 28, 2021.
International Search Report and Written Opinion of the International Searching Authority for International Application No. PCT/US2018/014014, dated Apr. 26, 2018.
Japanese Patent Application No. 2022-069905, Office Action, dated May 30, 2023.

\* cited by examiner

DRUG DELIVERY DEVICE WITH STERILE FLUID FLOWPATH AND RELATED METHOD OF ASSEMBLY

CROSS-REFERENCE TO RELATED APPLICATION

This is the United States national phase of International Patent Application No. PCT/US18/14014, filed Jan. 17, 2018, which claims priority to U.S. Provisional Patent Application No. 62/460,559, filed Feb. 17, 2017. The entire contents of each of the foregoing are expressly incorporated herein by reference.

FIELD OF DISCLOSURE

The present disclosure generally relates to drug delivery devices and, more particularly, drug delivery devices capable of being worn by a patient while a drug is delivered to the patient.

BACKGROUND

Parenteral delivery of various drugs, i.e., delivery by means other than through the digestive track, has become a desired method of drug delivery for a number of reasons. By bypassing the digestive system of the patient, one can avoid degradation of the active ingredients caused by the catalytic enzymes in the digestive tract and liver and ensure that a necessary amount of drug, at a desired concentration, reaches the targeted site. Furthermore, the growth in treatments involving biologics, which are typically injected in liquid form, has made parenteral delivery more prevalent.

Traditionally, manual syringes and injection pens have been used for parenteral delivery. These devices typically must be held in the hand of the patient or caregiver during injection of the drug. Some drugs due to their large dosage size and/or viscosity require delivery over a significant period of time. While it is possible to increase the flow rate to reduce the injection time for such drugs, high flow rates can cause pain or discomfort to the patient. Furthermore, the efficacy of some drugs depends on continuous delivery over several minutes or hours, or delayed delivery following a certain event such as a chemotherapy treatment. Performing an injection with a manual syringe or an injection pen that lasts more than 15 seconds is typically not practical, in part because such devices must be held steady relative to the patient's skin to avoid causing pain. Also, use of a manual syringe or injection pen requires the patient to be immobile over the course of the injection, which may have a detrimental impact on the patient's lifestyle, particularly if the injection must take place over several minutes or hours.

On-body injectors and ambulatory infusion pumps which can be worn on a patient's skin or clothing make long duration injections more feasible. These wearable drug delivery devices have grown in preference because the patient or caregiver may not be required to interact with the device after it is placed onto the patient's body and activated. For some patients this removes the fear associated with manually inserting a needle or depressing a syringe plunger.

Wearable drug delivery devices typically have a planar or low profile shape so that the device is not an impediment to the patient's movement. To achieve this shape, the drug container within the device may be arranged so that its longitudinal axis is substantially parallel to the patient's skin when the device is worn by the patient. As a result, the delivery needle or cannula may not be axially aligned with the drug container such as in an autoinjector or injection pen. Consequently, a fluid pathway assembly may be included to fluidly connect the delivery needle or cannula with the drug container.

A sterile fluid flow path must be established between the fluid pathway assembly and the drug container during drug delivery. Ensuring that this is the case can affect the assembly of the device. For example, the drug container may be filled and sealed under sterile conditions in one assembly environment, and the fluid pathway assembly may be constructed and packaged under sterile conditions in another assembly environment. Subsequently, the drug container and the fluid pathway assembly may be assembled together with other components of the drug delivery device in another assembly environment. To reduce costs, the final assembly environment may be operated under non-sterile or non-aseptic conditions. Consequently, a risk exists that microbes or other contaminants in the final assembly environment will contaminate the exterior connection surfaces of the drug container and/or the fluid pathway assembly. This contamination may compromise the sterility of the fluid flow path to be established between the drug container and the fluid pathway assembly.

Some wearable drug delivery devices require the patient or caregiver, at the point of use, to insert the drug cartridge into the housing of the device and fluidly connect the drug cartridge with the fluid pathway assembly. This provides the patient or caregiver with the opportunity to clean the exterior connection surfaces of the drug cartridge and/or the fluid pathway assembly and thus remove any harmful microbes. However, such devices have the disadvantage of increasing the time and difficulty of preparing the device at the point of use, as well as increasing the likelihood of accidental spills of the drug. Furthermore, the caregiver and/or patient may require training to ensure that they install the drug cartridge properly. Thus, in at least some cases, it is preferable for the drug delivery device to be pre-filled and pre-loaded with the drug. However, this may preclude the opportunity to clean the exterior connection surfaces of the drug container and/or the fluid pathway assembly at the point of use.

The present disclosure sets forth drug delivery devices and related methods of assembly embodying advantageous alternatives to existing drug delivery devices and methods of assembly, and that may address one or more of the challenges or needs mentioned herein, as well as provide other benefits and advantages.

SUMMARY

One aspect of the present disclosure provides a drug delivery device including a housing defining an interior space, a container disposed in the interior space, a first seal member, a first removable membrane, a fluid pathway assembly, a second seal member, and a second removable membrane. The container may include a reservoir containing a drug and a stopper. The stopper may be movable through the reservoir from a proximal end of the reservoir toward a distal end of the reservoir to expel the drug from the reservoir during operation of the drug delivery device. The first seal member may be connected to the container at the distal end of the reservoir. The first removable membrane may cover an exterior surface of the first seal member to maintain sterility of the exterior surface of the first seal member prior to operation of the drug delivery device. The fluid pathway assembly may be configured to establish fluid communication with the reservoir during operation of the drug delivery device and have a first end, a second end, and a fluid passage extending between the first end and the second end. The second seal member may be connected to the first end of the fluid pathway assembly. The second removable membrane may cover an exterior surface of the second seal member to maintain sterility of the exterior surface of the second seal member prior to operation of the drug delivery device.

Another aspect of the present disclosure provides an arrangement for a drug delivery device. The arrangement may include a syringe, a seal member, and a removable membrane. The syringe may include a reservoir containing a drug, a needle having a first end in fluid communication with the reservoir and a second end extending outwardly from the reservoir, a stopper movable through the reservoir from a proximal end of the reservoir toward a distal end of the reservoir to expel the drug from the reservoir via the needle during operation of the drug delivery device. The seal member may be connected to the syringe at the distal end of the reservoir. The removable membrane may cover an exterior surface of the seal member to maintain sterility of the exterior surface of the seal member prior to operation of the drug delivery device.

Yet another aspect of the present disclosure provides an arrangement for a drug delivery device. The arrangement may include a fluid pathway assembly, a container access needle fixed relative to the fluid pathway assembly, and a removable membrane. The fluid pathway assembly may include a first end, a second end connectable to an interior element of the drug delivery device, a fluid passage extending between the first end and the second end, and a seal member connected to the first end of the fluid pathway assembly. The container access needle may have a first end and a second end, the second end being in fluid communication with the fluid passage. The removable membrane may cover an exterior surface of the seal member to maintain sterility of the exterior surface of the seal member prior to operation of the drug delivery device.

An additional aspect of the present disclosure provides a method of assembling a drug delivery device. The method may include: (a) providing a first housing portion and a second housing portion; (b) connecting a first pre-assembled arrangement to the first housing portion or the second housing portion, the first pre-assembled arrangement including a container having a reservoir containing a drug and a stopper, the stopper being movable through the reservoir from a proximal end of the reservoir toward a distal end of the reservoir to expel the drug from the reservoir during operation of the drug delivery device, a first seal member connected to the container at the distal end of the reservoir, and a first removable membrane covering an exterior surface of the first seal member to maintain sterility of the exterior surface of the first seal member prior to operation of the drug delivery device; and (c) connecting a second pre-assembled arrangement to the first housing portion or the second housing portion under non-sterile or non-aseptic conditions, the second pre-assembled arrangement including a fluid pathway assembly having a first end, a second end, and a fluid passage extending between the first end and the second end, a second seal member connected to the first end of the fluid pathway assembly, and a second removable membrane covering an exterior surface of the second seal member to maintain sterility of the exterior surface of the second seal member prior to operation of the drug delivery device.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the exemplary embodiments, except as may be explicitly delineated in the corresponding written description. Also, none of the drawings is necessarily to scale.

DETAILED DESCRIPTION

In general, the present disclosure relates to establishing and maintaining the sterility of an internal fluid flow path of a drug delivery device. The drug delivery device may include a drug container and a fluid pathway assembly that provides fluid communication between a reservoir of the drug container and other components or assemblies of the drug delivery device during operation of the device. Prior to operation, removable membranes may cover exterior connection surfaces of the drug container and the fluid pathway assembly, through which a sterile fluid flow path is to be later established. The removable membranes advantageously inhibit or prevent contamination of these surfaces. Immediately prior to or during operation of the device, the removable membranes may be detached from the drug container and the fluid pathway assembly. Thereafter, a sterile fluid flow path may be established between the drug container and the fluid pathway assembly. In some embodiments, to facilitate their removal, the removable membranes may each have a folded configuration which allows them to unroll when pulled away from the drug container or the fluid pathway assembly.

So configured, the removable membranes of the present disclosure advantageously reduce the cleanliness requirements for the assembly environment in which the drug container and the fluid pathway assembly are mounted to the remainder of the drug delivery device. This is because the removable membranes protect the exterior connection surfaces of the drug container and the fluid pathway assembly from microbes and other contaminants that may exist in the assembly environment. Accordingly, there may not be a need to operate the assembly environment as a sterile or aseptic clean room. This results in cost and/or time savings, and may facilitate the construction of the drug delivery device as a pre-filled and/or pre-loaded device that requires little or no assembly on behalf of the user (e.g., a patient or a caregiver).

Each of the foregoing components of the drug delivery device and the methods of assembling such a device will now be described in more detail.

Figure 1:
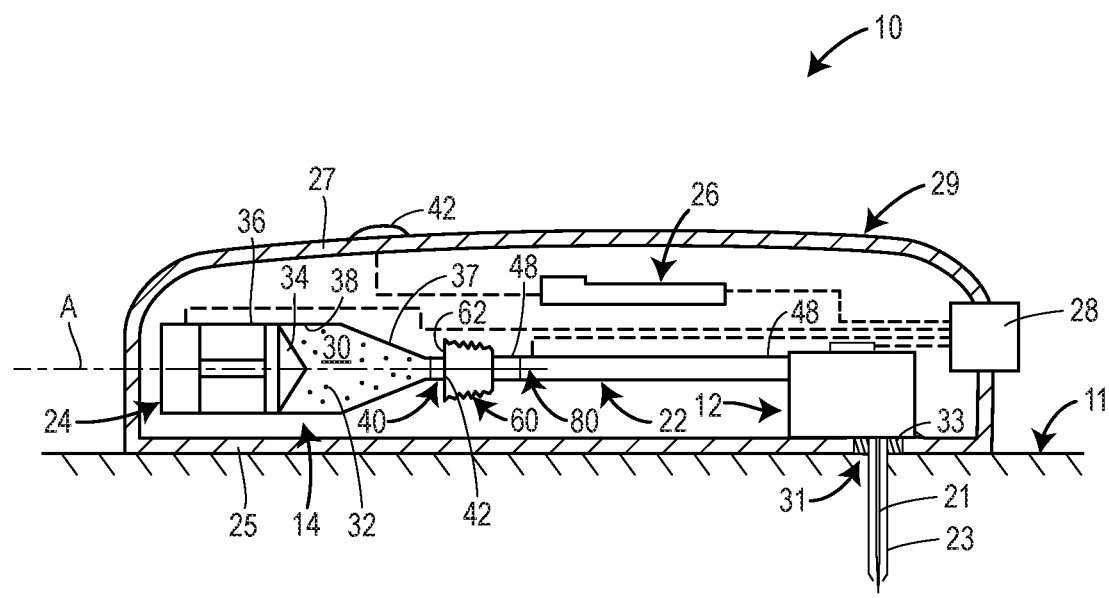
FIG. 1 illustrates a schematic cross-sectional view of an embodiment of a drug delivery device in accordance with principles of the present disclosure.

FIG. 1 illustrates one embodiment of a drug delivery device 10 in accordance with the present disclosure. As shown in FIG. 1, the drug delivery device 10 may be operated to subcutaneously deliver a drug to a patient. In the illustrated embodiment, the drug delivery device 10 is configured as a wearable drug delivery device such as an on-body injector or an ambulatory infusion pump, which is releasably attached to the patient's tissue 11 (e.g., the patient's skin). In other embodiments (not illustrated), the drug delivery device 10 may be configured as an autoinjector or injection pen which is temporarily held against the patient's tissue 11 over the course of the injection. The drug delivery device 10 may be configured to automatically deliver a fixed or a patient/operator-settable dose of the drug over a controlled or selected period of time. Furthermore, the drug delivery device 10 may be intended for self-administration by the patient, or may be operated by a formally trained healthcare professional or other caregiver to administer the injection.

Generally, the drug delivery device 10 may include an insertion mechanism 12, a container 14, a fluid pathway assembly 22, a drive mechanism 24, and a controller 26, each of which may be disposed within an interior space of a main housing 29. An actuator 28 (e.g., a depressible button) may protrude through an exterior surface of the housing 29 and may be configured to initiate operation of the drug delivery device 10 by activating, via mechanical and/or electrical means (shown in dotted lines in FIG. 1), the insertion mechanism 12, the fluid pathway assembly 22, the drive mechanism 24, the controller 26, and/or other mechanisms and/or electronics. In some embodiments, depressing the actuator 28 may only initiate operation of the controller 26, which in turn may execute programmable instructions to control operation of the insertion mechanism 12, the drive mechanism 24, and/or the fluid pathway assembly 22. In such embodiments, the controller 26 may include a processor (e.g., a microprocessor) and a non-transitory memory for storing the programmable instructions to be executed by the processor.

Still referring to FIG. 1, the housing 29 may include a bottom wall 25 configured to be releasably attached (e.g., adhered with an adhesive) to the patient's tissue 11, and a top wall 27 including one or more visual indicators 42 (e.g., lights, graphical displays, etc.) and/or a window (not illustrated) for viewing the container 14. The one or more visual indicators 42 may be used to communicate information to the user about the operational state of the drug delivery device 10 and/or condition of the drug 32. An opening 31 may be formed in the bottom wall 25, and optionally a septum 33 (e.g., a pierceable sterile barrier) may extend across the opening 31 to seal the interior of the housing 29 prior to use. In some embodiments, the septum 33 may be omitted, and instead a removable sealing member (not illustrated) may cover and seal closed the opening 31.

After the bottom wall 25 of the housing 29 is attached to the patient's tissue 11, the insertion mechanism 12 may be activated to insert a trocar 21 and a hollow cannula 23 surrounding the trocar 21 through the septum 33 and into the patient's tissue 11, as illustrated in FIG. 1. Immediately thereafter, the insertion mechanism 12 may automatically retract the trocar 21, leaving the distal open end of the cannula 23 inside the patient for subcutaneous delivery of the drug 32. The trocar 21 may be solid and have a sharpened end for piercing the patient's skin 11. Furthermore, the trocar 21 may be made of a more rigid material than the cannula 23. In some embodiments, the trocar 21 may be made of metal, whereas the cannula 23 may be made of plastic or another polymer. The relative flexibility of the cannula 23 may allow it to be disposed subcutaneously within the patient's tissue 11 for a period of a time without causing pain or significant discomfort to the patient. In other embodiments (not illustrated), the trocar 21 and cannula 23 may be omitted, and instead the insertion mechanism 12 may insert only a rigid, hollow needle into the patient for subcutaneous delivery of the drug 32.

In some embodiments, the insertion mechanism 12 may include one or more springs (e.g., coil springs, torsion springs, etc.) initially retained in an energized state, and which are released upon depression of the actuator 28 in order to insert the trocar 21 and cannula 23, or hollow needle, into the patient. Furthermore, retraction of the trocar 21 may be achieved by the automatic release of another spring after the trocar 21 and cannula 23 have been inserted into the patient. Other power sources for insertion and/or retraction are possible, including, for example, an electric motor, a hydraulic or pneumatic pump, or a canister that releases a pressurized gas or pressurized liquid to provide actuation energy.

With continued reference to FIG. 1, the container 14 may include a reservoir 30 containing a volume of the drug 32. In some embodiments, the reservoir 30 may be pre-filled with the drug 32 by a manufacturer. In some embodiments, the container 14 may be rigidly connected to the housing 29 such that the container 14 cannot move relative to the housing; whereas, in other embodiments, the container 14 may be slidably connected to the housing 29 such that the container 14 can move relative to the housing 29 during operation of the drug delivery device 10. The reservoir 30 may have an elongate, barrel-like shape extending along a longitudinal axis A. In embodiments where the drug delivery device 10 is configured as an on-body injector, the longitudinal axis A of the reservoir 30 may be perpendicular or substantially perpendicular, or otherwise non-parallel, to a direction in which the insertion mechanism 12 inserts a delivery member such as the cannula 23 into the patient. Initially, a stopper 34 or other piston member may be positioned in a proximal end 36 of the reservoir 30. The stopper 34 may sealingly and slidably engage an interior surface of a wall 38 of the container 14, and may be movable relative to the wall 38 of the container 14.

During operation of the drug delivery device 10, the drive mechanism 24 may push the stopper 34 along the longitudinal axis A from the proximal end 36 of the reservoir 30 to the distal end 37 of the reservoir 30 in order to expel the drug 32 from the reservoir 30. In some embodiments, the drive mechanism 24 may include one or more springs (e.g., coil springs, torsion springs, etc.) initially retained in an energized state, and which are released upon depression of the actuator 28. Following their release, the spring(s) may expand and move the stopper 34 through the reservoir 30 along the longitudinal axis A from the proximal end 36 to the distal end 37. In other embodiments, the drive mechanism 24 may include an electric motor (not illustrated) which rotates a gear mechanism to cause axial motion of the stopper 34 through the reservoir 30. In still further embodiments, the drive mechanism 24 may include both an electric motor and spring(s), wherein the electric motor regulates expansion of the spring(s) via a tether or pulley system. In still further embodiments, the drive mechanism 24 may include a canister that releases a pressurized gas or pressurized liquid to provide actuation energy.

At the distal end 37 of the reservoir 30, the container 14 may include an opening through which the drug 32 can be expelled during operation of the drug delivery device 10. Prior to operation of the drug delivery device 10, this opening may be covered and sealed closed by a first seal member 40 connected to the container 14 at the distal end 37 of the reservoir 30. Generally, the first seal member 40 may be configured to control access to the drug 32 in the reservoir 30. During operation, the first seal member 40 may be physically altered to permit fluid communication with the drug 32 in the reservoir 30. In embodiments where the container 14 is configured as an ampoule, such as the embodiments illustrated FIGS. 1 and 2A-4C, the first seal member 40 may be a septum constructed of a flexible and fluid impermeable material, such as rubber, for example, which is capable of being penetrated or pierced by the point or sharpened end 82 of a container access needle 80 mounted on the fluid pathway assembly 22. In such embodiments, the first seal member 40 may be clamped or adhered directly to the wall 38 of the container 14, such that the first seal member 40 covers an opening formed in the wall 38 of the container 14, wherein the opening is distal to and provides access to the distal end 37 of the reservoir 30.

In other embodiments, which are described in more detail below with reference to FIGS. 5A-7C, the container 14 may be configured as a syringe (e.g., a pre-filled syringe). In such embodiments, a rigid, hollow container needle 70 may extend through the wall 38 of the container 14, and have a first end 72 in fluid communication with the reservoir 30 and a second end 74, which may be sharpened, extending from the container 14 (see FIGS. 5A-7C). The container needle 70 may be rigidly connected to the wall 38 of the container 14 such that the container needle 70 cannot move relative to the container 14. Here, the wall 38 of the container 14 may function as a mounting member for rigidly connecting the container needle 70 to the container 14. In such embodiments, the first seal member 40 may cover an opening formed in the second end 74 of the container needle 70 protruding outwardly from the container 14. Furthermore, the first seal member 40 may be directly connected to the wall 38 of the container 14 or indirectly connected to the container 14 via mounting on the container needle 70. Furthermore, in such embodiments, the first seal member 40 may be constructed as a deformable septum, or as a collapsible or rigid sleeve defining a sterile interior chamber enclosing the exposed second end 74 of the container needle 70.

Referring to FIG. 1, the fluid pathway assembly 22 may be configured to establish fluid communication between the container 14 and the insertion mechanism 12 via a sterile fluid flow path during operation of the drug delivery device 10. Prior to use of the drug delivery device 10, the fluid pathway assembly 22 may not be in fluid communication with the container 14. During setup of the drug delivery device 10, or during the initial stages of operation of the drug delivery device 10 prior to drug delivery, the user may manually, or the drug delivery device 10 may automatically, enable, connect, or open the necessary connections to establish fluid communication between the container 14 and the fluid pathway assembly 22. Subsequently, the drive mechanism 24 may force the drug 32 stored in the container 14 through the sterile fluid flow path of the fluid pathway assembly 22 and into the cannula 23 or needle of the insertion mechanism 12 for subcutaneous delivery to the patient.

In some embodiments, the fluid pathway assembly 22 may be rigidly connected to the housing 29 such that the fluid pathway assembly 22 cannot move relative to the housing; whereas, in other embodiments, the fluid pathway assembly 22 may be slidably connected to the housing 29 such that the fluid pathway assembly 22 can move relative to the housing 29 during operation of the drug delivery device 10.

The fluid pathway assembly 22 may include a first end 44 having an opening, a second end 48 fluidly connected to the insertion mechanism 12, and a fluid passage 50 extending between the first end 44 and the second end 48. The fluid passage 50 may be sterilized, and may be partially or entirely made of a flexible tubing 52. Initially, there may be slack in the flexible tubing 52 to allow the fluid pathway assembly 22 to move relative to the housing 29 and/or to allow components of the insertion mechanism 12 to which the fluid pathway assembly 22 is attached to move relative to the housing 29. In some embodiments, the fluid passage 50 may include a rigid fluid restrictor element (not illustrated) in addition to the flexible tubing 52. The fluid restrictor element may have a smaller inner diameter than that of the flexible tubing 52 in order to regulate the flow rate of the drug 32 as it passes through the fluid pathway assembly 22. Furthermore, the fluid restrictor element may be made of a more rigid material than the flexible tubing 52. For example, the fluid restrictor element made be made of metal, whereas the flexible tubing 52 may be made of a polymeric material such as plastic.

Prior to operation of the drug delivery device 10, the opening at the first end 44 of the fluid pathway assembly 22 may be covered and initially sealed closed by a second seal member 60 which is connected to the first end 44 of the fluid pathway assembly 22. In a general sense, the second seal member 60 may be configured to control access to the fluid passage 50. During operation, the second seal member 60 may be physically altered to permit fluid communication with the fluid passage 50. The second seal member 60 may be axially aligned with the first seal member 40 such that an exterior end surface 61 of the second seal member 60 faces an exterior end surface 41 of the first seal member 40. In some embodiments, both the first and second seal members 40 and 60 may be axially aligned along the longitudinal axis A of the reservoir 30. Additionally, in some embodiments, a container needle 70 or a container access needle 80 (described below) may be axially aligned along the longitudinal axis A of the reservoir 30.

In the embodiments illustrated in FIGS. 1 and 2A-4C, a rigid, hollow container access needle 80 may extend from the first end 44 of the fluid pathway assembly 22. In some embodiments, the container access needle 80 may have a first end 82, which may be sharpened, protruding from the first end 44 of the fluid pathway assembly 22, and a second end 84 in fluid communication with the fluid passage 50. The first end 82 of the container access needle 80 may have an opening that is initially covered and sealed by the second seal member 60. In some embodiments, the fluid pathway assembly 22 may include a mounting member 86 or connection hub for rigidly connecting the container access needle 80 to the remainder of the fluid pathway assembly 22, so that the container access needle 80 cannot move relative to the fluid pathway assembly 22, and so that to the extent that the fluid pathway assembly 22 moves relative to the housing 29 the fluid pathway assembly 22 and the container access needle 80 move together jointly as a single unit relative to the housing 29. Furthermore, the second seal member 60 may be mounted on the container access needle 80 so that the second seal member 60 is connected to the first end 44 of the fluid pathway assembly 22 by way of the container access needle 80. Furthermore, in such embodiments, the second seal member 60 may be constructed as a deformable septum, or as a collapsible or rigid sleeve defining a sterile interior chamber enclosing the exposed first end 82 of the container access needle 80, as described below in more detail.

In other embodiments, such as the ones shown in FIGS. 5A-7C, the container access needle 80 may be omitted. In such embodiments, the second seal member 60 may be connected directly to the first end 44 of the fluid pathway assembly 22, and may cover and initially seal closed an opening formed in the first end 44 of the fluid pathway assembly 22. In such embodiments, the second member 60 may be a septum constructed of a flexible and fluid impermeable material, such as rubber, for example, which is capable of being penetrated or pierced by the point or sharpened end 74 of the container needle 70 mounted on the container 14 (e.g., the container needle 70). In such embodiments, the second seal member 60 may be clamped or adhered directly to first end 44 of the fluid pathway assembly 22.

As shown in FIG. 1, during operation of the drug delivery device 10, an exterior end surface 41 of the first seal member 40 may firmly and/or flushly engage an exterior end surface 61 of the second seal member 60. Accordingly, at this time, there may be little risk of microbes or other contaminants, airborne or stationary, within the housing 29 from contaminating the interface between the first seal member 40 and the second seal member 60. However, prior to operation of the drug delivery device 10, this may not be the case. Before operation, the exterior end surface 41 of the first seal member 40 may spaced apart from, or at least not firmly pressed against, the exterior end surface 61 of the second seal member 60. As such, there may be an opportunity for contaminants to infect the exterior end surface 41 of the first seal member 40 and/or the exterior end surface 61 of the second seal member 60. This contamination risk is particularly high if the container 14 and the fluid pathway assembly 22 are installed in the housing 29 in a non-sterile or non-aseptic assembly or manufacturing environment. Moreover, even if the exterior end surfaces 41 and 61 are assembled in such a manner that they flushly engage each other with no gap therebetween, a risk for contamination nevertheless exists if the assembly environment is not sterile or aseptic. Any microbes or contaminants disposed on the exterior end surfaces 41 and 61 as a result of the assembly process have a chance at being transferred into the reservoir 30 and/or the fluid passage 50 when the container needle 70 or the container access needle 80 penetrates the first seal member 40 and/or the second seal member 60 during operation of the drug delivery device 10. Accordingly, contaminants disposed on the exterior end surfaces 41 and 61 may compromise the sterility of the fluid flow path to be established between the container 14 and the patient during drug delivery.

Figure 2A:
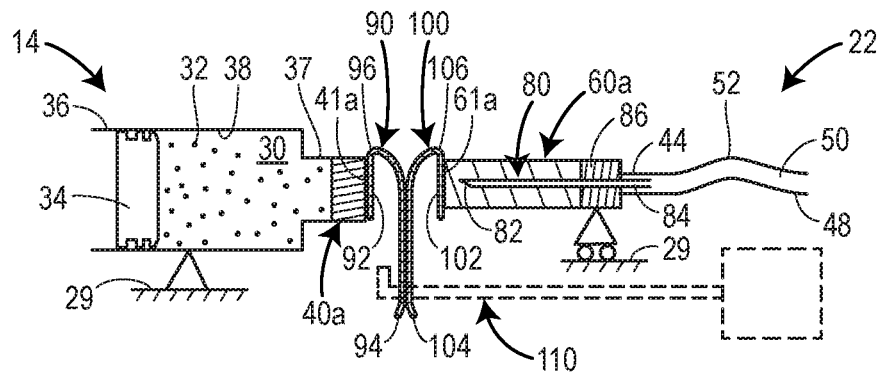
FIGS. 2A-2C depict a schematic cross-sectional view of a sequence of steps involved in establishing fluid communication between a container and a fluid pathway assembly according to one embodiment of the present disclosure.

To address this problem, and with reference to FIG. 2A, removable membranes 90 and 100 may cover, respectively, the exterior end surface 41 of the first seal member 40 and the exterior end surface 61 of the second seal member 60, in order to maintain sterility of these surfaces during assembly of the drug delivery device 10 and prior to establishment of fluid communication between the container 14 and the fluid pathway assembly 22 (e.g., during storage of the drug delivery device 10 after assembly and prior to use). Each of the removable membranes 90 and 100 may function as a sterile barrier that prevents or inhibits microbes and other contaminants from contaminating the exterior end surface 41 or the exterior end surface 61.

In some embodiments, the removable membranes 90 and 100 may be removably attached to, respectively, the exterior end surfaces 41 and 61 via an adhesive. Alternatively or additionally, fasteners or clamps may be used to removably attach the removable membranes 90 and 100 to their respective exterior end surfaces 41 and 61. In some embodiments, the adhesive may include an antimicrobial, antibacterial, and/or antiviral agent to further protect against contamination of the exterior end surfaces 41 and 61. Removal of the removable membranes 90 and 100 from the first and second seal member 40 and 60 may be accomplished manually or automatically via a membrane removal member 110 incorporated into the drug delivery device 10, as described below in more detail.

The material used to construct each of the removable membranes 90 and 100 may have a thickness T that is less than or equal to approximately (e.g., ±10%) 2.0 mm, or less than or equal to approximately (e.g., ±10%) 1.0 mm, or less than or equal to approximately (e.g., ±10%) 0.5 mm, or less than or equal to approximately (e.g., ±10%) 0.25 mm, or less than or equal to approximately (e.g., ±10%) 0.1 mm, or less than or equal to approximately (e.g., ±10%) 0.05 mm, or within a range equal to approximately (e.g., ±10%) 0.01 mm-0.25 mm. In some embodiments, the removable membranes 90 and 100 may each be constructed of thin piece of plastic, paper, laminated paper, and/or rubber. Furthermore, in some embodiments, each of the removable membranes 90 and 100 may be made of an electrically conductive material, such as a thin metal foil, for example. In such embodiments, the electrical conductivity of the removable membranes 90 and 100 may be utilized to detect their removal from the first and second seal members 40 and 60. For example, removal of the removable membranes 90 and 100 may interrupt, or alternatively enable, the flow of electricity through a sensor (e.g., a sensing circuit) for detecting the position of the removable membranes 90 and 100. A determination by the sensor that the removable membranes 90 and 100 have been removed, in turn, can be used by the controller 26 to determine an operational state (e.g., "ready for delivery") of the drug delivery device 10. In some embodiments, the one or more visual indicators 42 may be operated to communicate the operational state to the user of the drug delivery device 10.

As shown in FIG. 2A, each of the removable membranes 90 and 100 may initially have a folded configuration prior to their removal from their respective ones of the first and second seal members 40 and 60. The folded configuration of each of the removable membranes 90 and 100 may facilitate their removal from the first and second seal members 40 and 60. More particularly, with reference to FIG. 2B, the folded configuration may permit each of the removable membranes 90 and 100 to unroll from the seal members 40 and 60 when the removable membranes 90 and 100 are pulled in a linear or substantially linear direction away from their respective seal members 40 and 60. This unrolling action may reduce the amount of force needed remove the removable membranes 90 and 100, particularly if an adhesive is used to connect the removable membranes 90 and 100 to their respective seal members 40 and 60. This is because the removal force will not be required to overcome the entirety of the adhesive force all at once. Rather, the removal force can gradually overcome the adhesive force as the removable membrane 90 or 100 peels away from its respective seal member 40 or 60. Moreover, a lower removal force may reduce the risk of tearing of the removable membranes 90 and 100 as they are detached. Still further, to the extent that the removable membranes 90 and 100 are initially compressed between the first and second seal members 40 and 60, the unrolling action enabled by the folded configuration may be helpful in reducing the effects of frictional resistance caused by this compression. Additionally, the dual unrolling action may occur simultaneously and with each removable membrane 90 and 100 unrolling at the same or substantially the same rate. Accordingly, there may be little or no risk of contact between the exterior surfaces of the second ends 94 and 104 of the removable membranes 90 and 100, which may be non-sterile, and exterior end surfaces 41 and 61 of the seal members 40 and 60, which may be sterile.

Referring to FIG. 2A, the removable membrane 90 may include: a first end 92 covering and directly contacting the exterior end surface 41 of the first seal member 40, a second end 94 folded over and covering the first end 92, and a bent or folded portion 96 in between and connecting the first end 92 and the second end 94. Similarly, the removable membrane 100 may include: a first end 102 covering and directly contacting the exterior end surface 61 of the second seal member 60, a second end 104 folded over and covering the first end 102, and a bent or folded portion 106 connecting the first end 102 and the second end 104. In some embodiments, the container 14 and the fluid pathway assembly 22 may be installed in the drug delivery device 10 such that the second end 94 of the removable membrane 90 and the second end 104 of the removable membrane 100 directly contact each other prior to use of the drug delivery device 10. In other embodiments, the container 14 and the fluid pathway assembly may be installed in the drug delivery device 10 such that the second end 94 of the removable membrane 90 and the second end 104 of the removable membrane 100 are spaced apart, but immediately adjacent, to each other prior to use of the drug delivery device 10. In such embodiments, the container 14 and the fluid pathway assembly 22 may be moved toward each other during the initial stages of operation of the drug delivery device 10 such that the second end 94 of the removable membrane 90 and the second end 104 of the removable membrane 100 are brought in contact with each other.

Figure 8:
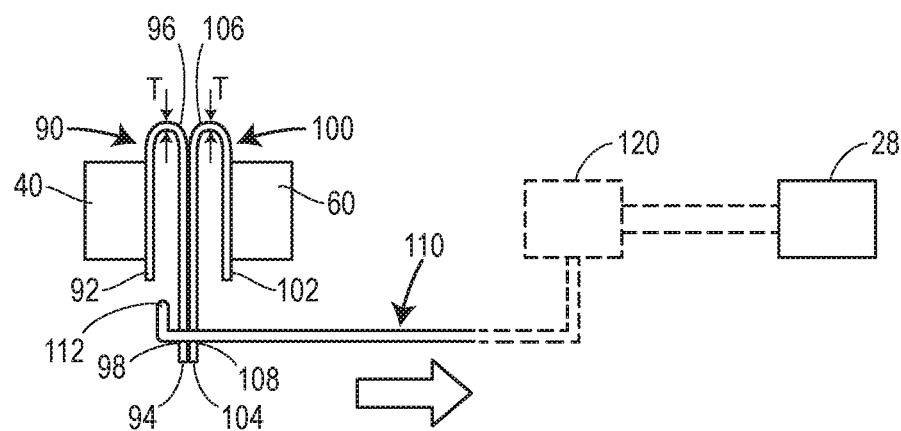
FIG. 8 illustrates a schematic side view of one embodiment of a membrane removal member according to the present disclosure.

Briefly turning to FIG. 8, in some embodiments, the second end 94 of the removable membrane 90 and the second end 104 of the removable membrane 100 may each function as a pull tab for removing their respective removable membrane 90 and 100 from the first and second seal members 40 and 60. As such, each of the second ends 94 and 104 may be configured to be gripped and pulled by the membrane removal member 110. As shown in FIG. 8, this may entail each of the second ends 94 and 104 having a respective hole 98 or 108 extending therethrough so that the membrane removal member 110 can be connected to each of the second ends 94 and 104. In such embodiments, the membrane removal member 110 may extend thorough the holes 98 and 108, and include a catch member 112 such as a hook at its terminal end which extends in a direction perpendicular or substantially perpendicular, or otherwise non-parallel, to the portion of the membrane removal member 110 passing through the holes 98 and 108. This may allow the catch member 112 to pull the removable membranes 90 and 100 with it when the membrane removal member 110 is actuated in the direction of the arrow shown in FIG. 8.

In the embodiment shown in FIG. 8, the membrane removal member 110 may be operatively connected to the actuator 28 such that manual displacement (e.g., depression) of the actuator 28 by the user may cause the membrane removal member 110 to move in a direction which pulls the removable membranes 90 and 100 away from their respective seal members 40 and 60. In some embodiments, a motion conversion mechanism 120, including one or more gears for example, may be connected between the actuator 28 and the membrane removal member 110 to convert movement of the actuator 28 in one direction into movement of the membrane removal member 110 in a different direction. In other embodiments, the motion conversion mechanism 120 may be omitted and movement of the actuator 28 in one direction may cause movement of the membrane removal member 110 in the same direction.

In alternative embodiments, the membrane removal member 110 may be operatively connected to the drive mechanism 24 instead of the actuator 28. Actuation movement of the membrane removal member 110 may be provided by the drive mechanism 24 in such embodiments. For example, the drive mechanism 24 may be an electric motor which outputs rotational movement, and that rotational movement may be converted by a motion conversion mechanism, including one or more gears and/or a pulley system for example, into linear translation of the membrane removal member 110.

Figure 9:
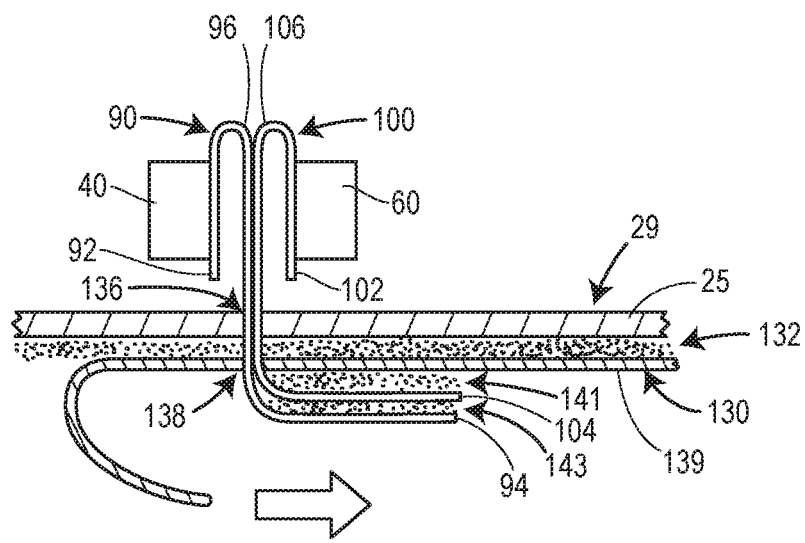
FIG. 9 depicts a schematic cross-sectional view of another embodiment of a membrane removal member according to the present disclosure.

Looking to FIG. 9, another embodiment of a membrane removal member 130 is depicted. The membrane removal member 130 may substituted for the membrane removal member 110 described above. Unlike the membrane removal member 110 which may be contained within the housing 29, the membrane removal member 130 may be disposed on the exterior of the housing 29. The membrane removal member 130 may correspond to an adhesive liner (e.g., a thin piece of plastic, paper, laminated paper, and/or rubber) which covers a skin adhesive 132 applied to the exterior surface of the bottom wall 25 of the housing 29 prior to use of the drug delivery device 10. In some embodiments, this adhesive liner may also function as a removable sterile barrier for the opening 31. In order to expose the skin adhesive 132 so that the drug delivery device 10 can be releasably attached to the patient's tissue 11, a user be required to peel away or otherwise remove the adhesive liner from the housing 29. The arrow depicted in FIG. 9 illustrates the peeling away movement of the adhesive liner. The first and second removable membranes 90 and 100 may be fixedly attached to the adhesive liner so that removable membranes 90 and 100 move together jointly with the adhesive liner when the adhesive liner is pulled away from the housing 29. More particularly, the second end 94 of the removable membrane 90 and the second end 104 of the removable membrane 100 may pass through a hole 136 formed in the bottom wall 25 of the housing 29, and through a hole 138 formed in the membrane removal member 130 (i.e., the adhesive liner). The second end 94 of the removable membrane 94 and the second end 104 of the removable membrane 100 may be folded over the bottom surface 139 of the membrane removal member 130 so that they lie flat or substantially flat on the bottom surface 139 of the membrane removal member 130. The second end 94 of the removable membrane 94 and/or the second end 104 of the removable membrane 100 may be adhered to the bottom surface 139 of the membrane removal member 130 to fixedly attach these elements together. In some embodiments, a first one of the second end 94 and the second end 104 may be adhered directly to the bottom surface 139 of the membrane removal member 130 (e.g., via adhesive layer 141), and a second one of the second end 94 and the second end 104 may be adhered directly to the first one of the second end 94 and the second end 104 (e.g., via adhesive layer 143), as shown in FIG. 9. Accordingly, when the user pulls away the membrane removal member 130 (i.e., the adhesive liner) to expose the skin adhesive 132, this movement may cause the membranes 90 and 100 to unroll from their respective first and second seal members 40 and 60. While the present embodiment utilizes an adhesive to fixedly connect the removable membranes 40 and 60 to the membrane removal member 130, alternative embodiments may use a mechanical fastener such as a pin for this purpose. Furthermore, in some embodiments, a portion of the removable membrane 90 initially disposed within the housing 29 and a portion of the removable membrane 100 initially disposed within the housing 29 may be attached to each other via an adhesive and/or a mechanical fastener such as a pin. In such an embodiment, it may only be necessary to attach a single one of the removable membranes 90 and 100 to the adhesive liner. Accordingly, this may allow for the removable membrane 100, the adhesive liner, and the bottom wall 25 of the housing 29 to be completely assembled prior to installation of the container 14, the first seal member 40, and the removable membrane 90, which need only be connected to the portion of the removable membrane 100 disposed within the housing 29.

In both the FIG. 8 and FIG. 9 embodiments, the membrane removal member 110 or 130 may translate in a linear or substantially linear direction during the removal operation. This direction of movement may be perpendicular or substantially perpendicular, or otherwise non-parallel, to the second end 94 of the removable membrane 90 and/or the second end 104 of the removable membrane 100. Furthermore, the direction of movement of the membrane removal member 110 or 130 during the removal operation may be perpendicular or substantially perpendicular, or otherwise non-parallel, to the exterior end surface 41 of the first seal member 40 and/or the exterior end surface 61 of the second seal member 60. Furthermore, in some embodiments, the direction of movement of the membrane removal member 110 or 130 may be parallel or substantially parallel to the longitudinal axis A of the reservoir 30. This movement of the membrane removal member 110 or 130 may allow for a more compact design of the drug delivery device 10. Nevertheless, in other embodiments, the direction of movement of the membrane removal member 110 or 130 during the removal operation may be parallel to the second end 94 of the removable membrane 90 and/or the second end 104 of the removable membrane 100.

Referring back to FIGS. 2A-7C, various embodiments of the first and second seal members 40 and 60 will now be described. The different embodiments of the first seal member 40 are indicated by the reference numeral "40" appended with one of the suffixes "a-f". Similarly, the different embodiments of the second seal member 60 are indicate by the reference numeral "60" appended with one of the suffixes "a-f". FIGS. 2A-4C illustrate embodiments where the container 14 is configured as an ampoule lacking the container needle 70 and the fluid pathway assembly 22 is mounted with the container access needle 80. By contrast, FIGS. 5A-7C illustrate embodiments where the container 14 is configured as a syringe mounted with the container needle 70 and the fluid pathway assembly 22 is not mounted with the container access needle 80. In the embodiments shown in FIGS. 2A-7C, the fluid pathway assembly 22 is slidably connected to the housing 29 such that the fluid pathway assembly 22 can move relative to the housing 29 during operation; whereas the container 14 is rigidly connected to the housing 29 so that the container 14 does not move relative to the housing 29 during operation. However, in alternative versions of any one of the embodiments illustrated in FIGS. 2A-7C, the container 14 may be slidably connected to the housing 29 such that the container 14 can move relative to the housing 29 during operation; whereas the fluid pathway assembly 22 may be rigidly connected to the housing 29 so that the fluid pathway assembly 22 does not move relative to the housing 29 during operation.

Figure 2B:
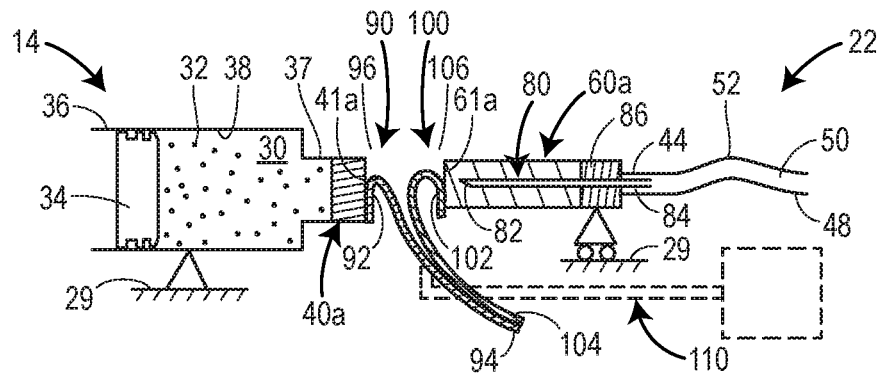
Figure 2C:
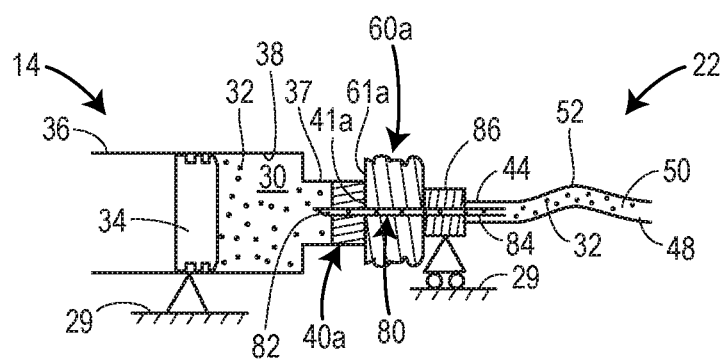

FIGS. 2A-2C illustrate an embodiment where each of the first seal member 40a and the second seal member 60a is defined by a respective pierceable septum. The septum defining the first seal member 40a may be constructed of a flexible and fluid impermeable material, such as rubber, for example, which is capable of being penetrated or pierced by the sharpened first end 82 of the container access needle 80 mounted on the fluid pathway assembly 22. The septum defining the second seal member 60a may be constructed of a deformable material whose axial length can be compressed or shortened during operation of the drug delivery device 10. More particularly, as shown in FIG. 2C (which corresponds to the stage of operation depicted in FIG. 1), during operation of the drug delivery device 10 the distance separating the container 14 and the fluid pathway assembly 22 may be decreased by moving the fluid pathway assembly 22 toward the container 14, or vice versa. As a result, the second seal member 60a may be pressed against the first seal member 40a and the deformable septum defining the second seal member 60a may decrease in length from the initial configuration shown in FIGS. 2A and 2B to the compressed configuration shown in FIG. 2C. Consequently, the sharpened end 82 of the container access needle 80, which initially may have been embedded within the material of the second seal member 60a (see FIG. 2A), may be pushed through the exterior end surface 61a of the second member 60a, then through the exterior end surface 41a of the first seal member 40a, and then into the reservoir 30 to establish fluid communication with the drug 32. In order to push the container access needle 80 through the deformable septum of the second seal member 60a, the mounting member 86 for the container access needle 80 may be constructed of a more rigid (e.g., less compressible) material than the deformable septum of the second seal member 60a. Accordingly, the mounting member 86 may not deform during deformation of the second seal member 60a. Furthermore, in some embodiments, the compressibility of the deformable septum of the second seal member 60a may be achieved by constructing the deformable septum partially or entirely of a spongy or porous material. Furthermore, the deformable septum may be configured to provide a sterile barrier for maintaining the sterility of the sharpened end 82 of the container access needle 80 while it is embedded within the material of the deformable septum prior to use of the drug delivery device 10. As shown in FIG. 2B, prior to the container access needle 80 accessing the reservoir 30, the membrane removal member 110 or 130 may be actuated to remove the removable membranes 90 and 100 from their respective first and second seal members 40a and 60a, in a manner consistent with the description above.

Figure 3A:
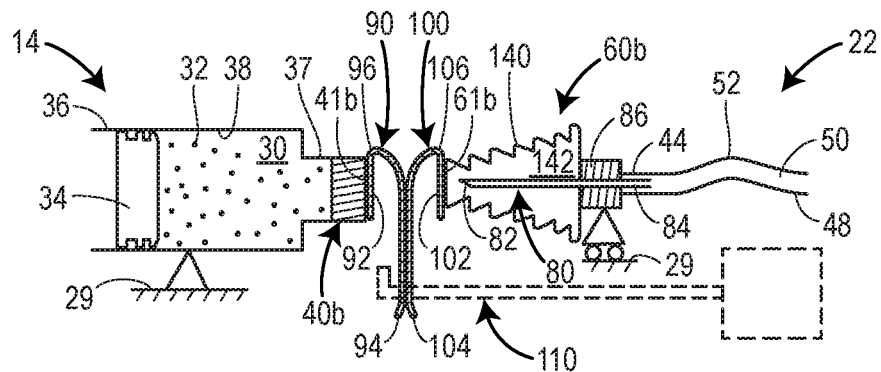
FIGS. 3A-3C illustrate a schematic cross-sectional view of a sequence of steps involved in establishing fluid communication between a container and a fluid pathway assembly according to another embodiment of the present disclosure.
Figure 3B:
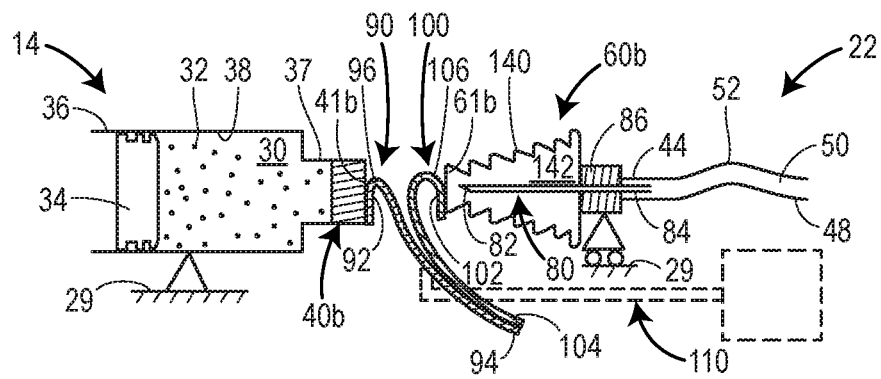
Figure 3C:
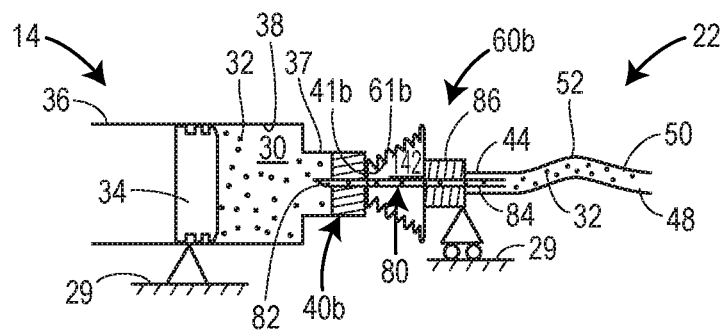

FIGS. 3A-3C depict an embodiment where the first seal member 40b is defined by a pierceable septum similar to the embodiment in FIGS. 2A-2C, and the second seal member 60b is defined by a corrugated sleeve 140 defining a sterile interior chamber 142. As shown in FIG. 3A, the sharpened end 82 of the container access needle 80 initially may be stored in the sterile interior chamber 142. In some embodiments, the removable membrane 100 may cover an opening formed in the exterior end surface 61 at an end of the corrugated sleeve 140 in order to seal closed the sterile interior chamber 142. In other embodiments, a cover member (not illustrated) positioned between the removable membrane 100 and the corrugated sleeve 140 may cover this opening, and may be pierced by the sharpened end 82 of the container access needle 80 during operation of the drug delivery device 10. The corrugated sleeve 140 may be configured so that its axial length can be compressed or shortened during operation of the drug delivery 10. This may be achieved by configuring the corrugated sleeve 140 with a plurality of alternating ridges and grooves which fold back on themselves when the corrugated sleeve 140 is pressed against the first seal member 40b. Also, to facilitate its collapse, the corrugated sleeve 140 may be cone-shaped, with the narrow end of the cone being connected to the fluid pathway assembly 22. More particularly, as shown in FIG. 3C, during operation of the drug delivery device 10 the distance separating the container 14 and the fluid pathway assembly 22 may be decreased by moving the fluid pathway assembly 22 toward the container 14, or vice versa. As a result, the second seal member 60b may be pressed against the first seal member 40b and the corrugated sleeve 140 defining the second seal member 60b may decrease in length from the initial configuration shown in FIGS. 3A and 3B to the compressed configuration shown in FIG. 3C. Consequently, the sharpened end 82 of the container access needle 80, which initially may have been stored within the sterile interior chamber 142 (see FIG. 3A), may be pushed outwardly through the exterior end surface 61b of the corrugated sleeve 140, then through the exterior end surface 41b of the first seal member 40b, and then into the reservoir 30 to establish fluid communication with the drug 32. In order to push the container access needle 80 through the corrugated sleeve 140, the mounting member 86 for the container access needle 80 may be constructed of a more rigid (e.g., less compressible) material than the corrugated sleeve 140. Accordingly, the mounting member 86 may not deform during deformation of the corrugated sleeve 140. As shown in FIG. 3B, prior to the container access needle 80 accessing the reservoir 30, the membrane removal member 110 or 130 may be actuated to remove the removable membranes 90 and 100 from their respective first and second seal members 40b and 60b, in a manner consistent with the description above.

Figure 4A:
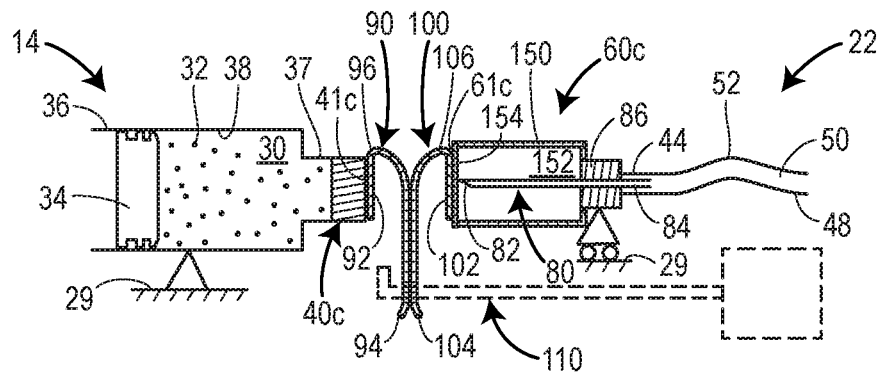
FIGS. 4A-4C depict a schematic cross-sectional view of a sequence of steps involved in establishing fluid communication between a container and a fluid pathway assembly according to another embodiment of the present disclosure.
Figure 4B:
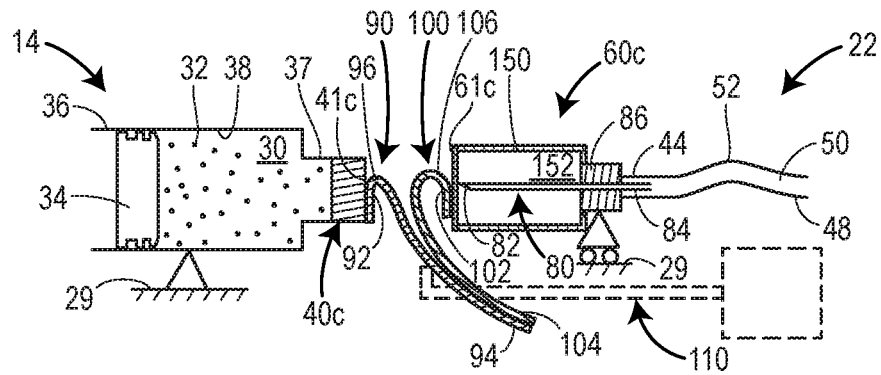
Figure 4C:
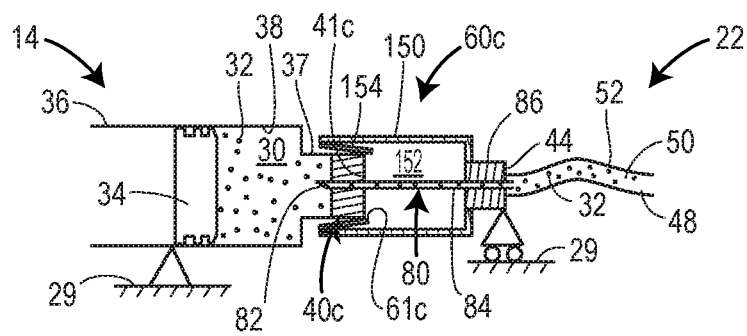

FIGS. 4A-4C depict an embodiment where the first seal member 40c is defined by a pierceable septum similar to the embodiments in FIGS. 2A-3C, and the second seal member 60c is defined by a rigid sleeve 150 defining a sterile interior chamber 152. As shown in FIG. 4A, the sharpened end 82 of the container access needle 80 initially may be stored in the sterile interior chamber 152. In some embodiments, the removable membrane 100 may cover an opening at an end of the rigid sleeve 150 opposite to an end of the rigid sleeve 150 attached to the fluid pathway assembly 22 in order to seal closed the sterile interior chamber 152. In other embodiments, a cover member 154 (e.g., a thin piece of plastic, paper, laminated paper, and/or rubber) positioned between the removable membrane 100 and the rigid sleeve 150 may cover this opening. Unlike the corrugated sleeve 140, the rigid sleeve 150 may not be compressed in length during operation of the drug delivery 10. Instead, the rigid sleeve 150 may be move toward the container 14 (or vice versa) such that the first seal member 40b moves into the sterile interior chamber 152 and is pierced by the sharpened end 82 of the container access needle 80 during operation of the drug delivery device 10. The cover member 154 may be deformed or penetrated by the first seal member 40c during this movement so that the first seal member 40c can enter the sterile interior chamber 152. More particularly, as shown in FIG. 4C, during operation of the drug delivery device 10 the distance separating the container 14 and the fluid pathway assembly 22 may be decreased by moving the fluid pathway assembly 22 toward the container 14, or vice versa. As a result, the first seal member 40c may enter the sterile interior chamber 152 of the rigid sleeve 150. The container access needle 80 may remain stationary relative to the rigid sleeve 150 during this movement. Consequently, the sharpened end 82 of the container access needle 80 may penetrate through the exterior end surface 41c of the first seal member 40c, and then into the reservoir 40 to establish fluid communication with the drug 32. As illustrated in FIG. 4B, prior to the container access needle 80 accessing the reservoir 30, the membrane removal member 110 or 130 may be actuated to remove the removable membranes 90 and 100 from their respective first and second seal members 40c and 60c, in a manner consistent with the description above.

Figure 5A:
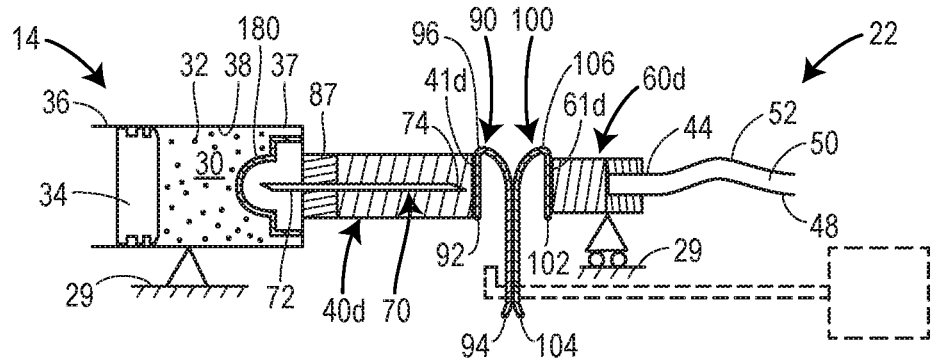
FIGS. 5A-5C illustrate a schematic cross-sectional view of a sequence of steps involved in establishing fluid communication between a container and a fluid pathway assembly according to another embodiment of the present disclosure.

Turning to FIGS. 5A-7C, illustrated are embodiments where the container access needle 80 is omitted and the container 14 is configured as a syringe mounted with the container needle 70. FIGS. 5A-5C illustrate an embodiment where each of the first seal member 40d and the second seal member 60d is defined by a respective pierceable septum. The septum defining the second seal member 60d may be constructed of a flexible and fluid impermeable material, such as rubber, for example, which is capable of being penetrated or pierced by the sharpened second end 74 of the container needle 70. The septum defining the first seal member 40d may be constructed of a deformable material whose axial length can be compressed or shortened during operation of the drug delivery device 10. More particularly, as shown in FIG. 5C, during operation of the drug delivery device 10 the distance separating the container 14 and the fluid pathway assembly 22 may be decreased by moving the fluid pathway assembly 22 toward the container 14, or vice versa. As a result, the first seal member 40d may be pressed against the second seal member 60d and the deformable septum defining the first seal member 40d may decrease in length from the initial configuration shown in FIGS. 5A and 5B to the compressed configuration shown in FIG. 5C. Consequently, the sharpened end 74 of the container needle 70, which initially may have been embedded within the material of the first seal member 40d (see FIG. 5A), may be pushed through the exterior end surface 41d of the first seal member 40d, then through the exterior end surface 61d of the second seal member 60d, and then into the fluid passage 50 to establish fluid communication between the reservoir 30 and the fluid passage 50. In order to push the container needle 70 through the deformable septum of the first seal member 40d, a mounting member 87 for the container needle 70 (which may correspond to the wall 38 of the container 14 or may be a separate component rigidly attached to the wall 38 of the container 14) may be constructed of a more rigid (e.g., less compressible) material than the deformable septum of the first seal member 40d. Accordingly, the mounting member 87 may not deform during deformation of the first seal member 40d. The mounting member 87 may rigidly connect the container needle 70 to the container 14, so that the container needle 70 cannot move relative to the wall 38 of the container 14, and so that to the extent that the container 14 moves relative to the housing 29 the container 14 and the container needle 70 move jointly as a single unit relative to the housing 29. Furthermore, in some embodiments, the compressibility of the deformable septum of the first seal member 40d may be achieved by constructing the deformable septum partially or entirely of a spongy or porous material. Furthermore, the deformable septum may be configured to provide a sterile barrier for maintaining the sterility of the sharpened end 74 of the container needle 70 while it is embedded within the material of the deformable septum prior to use of the drug delivery device 10. Furthermore, in some embodiments, the mounting member 86, which rigidly connects the second seal member 60d to the flexible tubing 52 of the fluid pathway assembly 22, may be constructed of a more rigid (e.g., less compressible) material than the corrugate sleeve 140, such that the mounting member 86 also does not deform during deformation of the corrugated sleeve 160. As shown in FIG. 5B, prior to the container needle 70 accessing the fluid passage 50, the membrane removal member 110 or 130 may be actuated to remove the removable membranes 90 and 100 from their respective first and second seal members 40d and 60d, in a manner consistent with the description above.

Figure 5B:
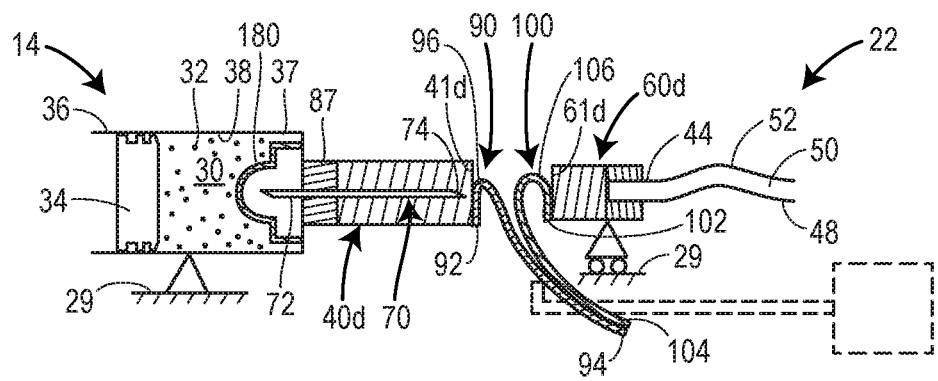
Figure 5C:
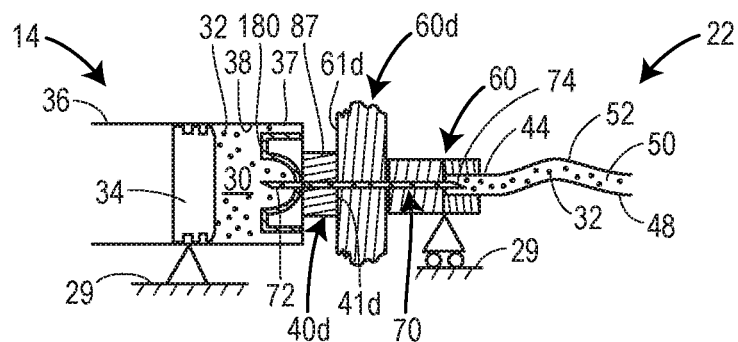
Figure 6A:
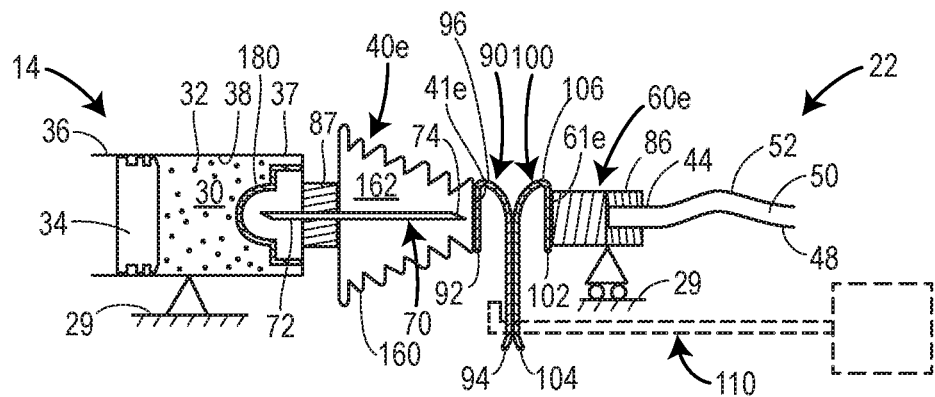
FIGS. 6A-6C depict a schematic cross-sectional view of a sequence of steps involved in establishing fluid communication between a container and a fluid pathway assembly according to another embodiment of the present disclosure.
Figure 6B:
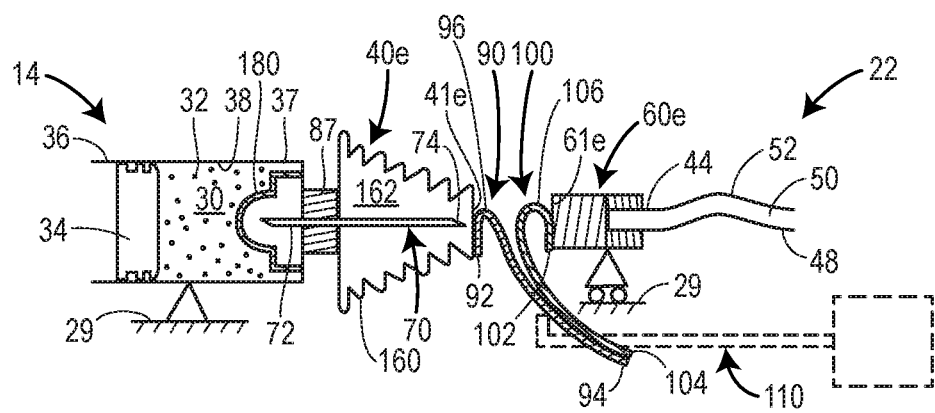
Figure 6C:
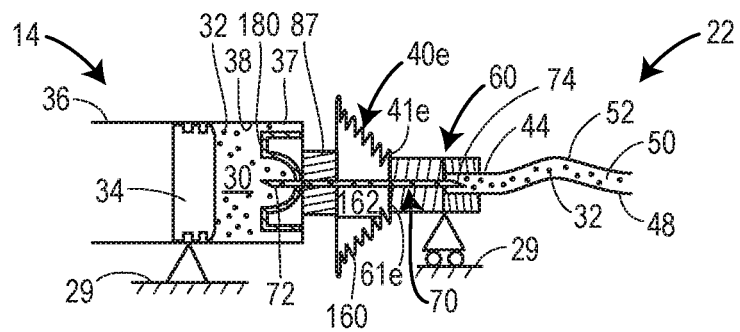

FIGS. 6A-6C depict an embodiment where the second seal member 60e is defined by a pierceable septum similar to the embodiment in FIGS. 5A-5C, and the first seal member 40e is defined by a corrugated sleeve 160 defining a sterile interior chamber 162. As shown in FIG. 6A, the sharpened end 74 of the container needle 70 initially may be stored in the sterile interior chamber 162. In some embodiments, the removable membrane 90 may cover an opening formed in the exterior end surface 61 of the corrugated sleeve 160 in order to seal closed the sterile interior chamber 162. In other embodiments, a cover member (not illustrated) positioned between the removable membrane 90 and the corrugated sleeve 160 may cover this opening, and may be pierced by the sharpened end 74 of the container needle 70 during operation of the drug delivery device 10. The corrugated sleeve 160 may be configured so that its axial length can be compressed or shortened during operation of the drug delivery 10. This may be achieved by configuring the corrugated sleeve 160 with a plurality of alternating ridges and grooves which fold back on themselves when the corrugated sleeve 160 is pressed against the second seal member 60e. Also, to facilitate its collapse, the corrugated sleeve 160 may be cone-shaped, with the narrow end of the cone being connected to the container 14. More particularly, as shown in FIG. 6C, during operation of the drug delivery device 10 the distance separating the container 14 and the fluid pathway assembly 22 may be decreased by moving the fluid pathway assembly 22 toward the container 14, or vice versa. As a result, the first seal member 40e may be pressed against the second seal member 60e and the corrugated sleeve 160 defining the first seal member 40e may decrease in length from the initial configuration shown in FIGS. 6A and 6B to the compressed configuration shown in FIG. 6C. Consequently, the sharpened end 74 of the container needle 70, which initially may have been stored within the sterile interior chamber 162 (see FIG. 6A), may be pushed outwardly through the exterior end surface 41e of the corrugated sleeve 160, then through the exterior end surface 61e of the second seal member 60e, and then into the fluid passage 50 to establish fluid communication between the reservoir 30 and the fluid passage 50. In order to push the container needle 70 through the corrugated sleeve 160, the mounting member 87 may be constructed of a more rigid (e.g., less compressible) material than the corrugated sleeve 140. Accordingly, the mounting member 87 (which may correspond to the wall 38 of the container 14 or may be a separate component rigidly attached to the wall 38 of the container 14) may not deform during deformation of the corrugated sleeve 160. Furthermore, in some embodiments, the mounting member 86, which rigidly connects the second seal member 60d to the flexible tubing 52 of the fluid pathway assembly 22, may be constructed of a more rigid (e.g., less compressible) material than the corrugate sleeve 140, such that the mounting member 86 also does not deform during deformation of the corrugated sleeve 160. As shown in FIG. 6B, prior to the container needle 70 accessing the fluid passage 50, the membrane removal member 110 or 130 may be actuated to remove the removable membranes 90 and 100 from their respective first and second seal members 40e and 60e, in a manner consistent with the description above.

Figure 7A:
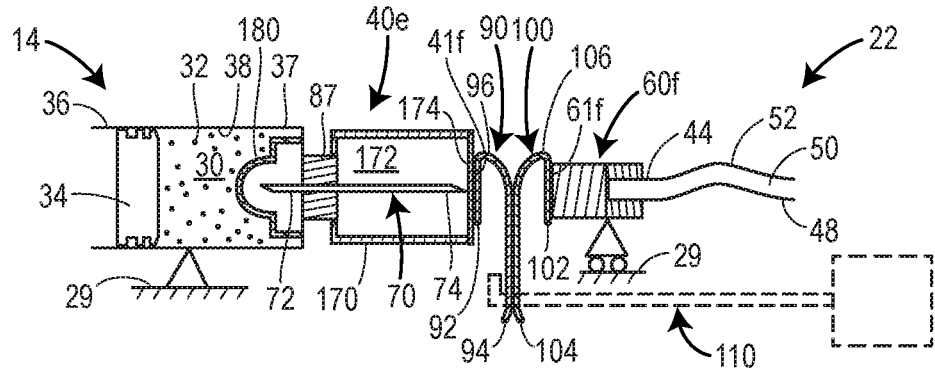
FIGS. 7A-7C illustrate a schematic cross-sectional view of a sequence of steps involved in establishing fluid communication between a container and a fluid pathway assembly according to another embodiment of the present disclosure.
Figure 7B:
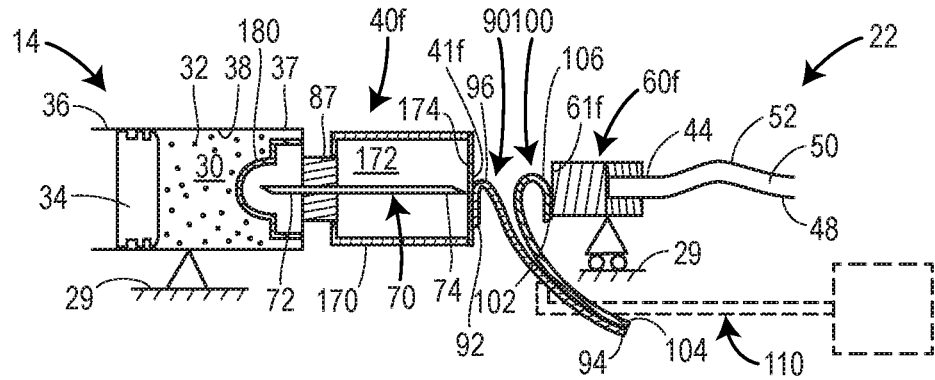
Figure 7C:
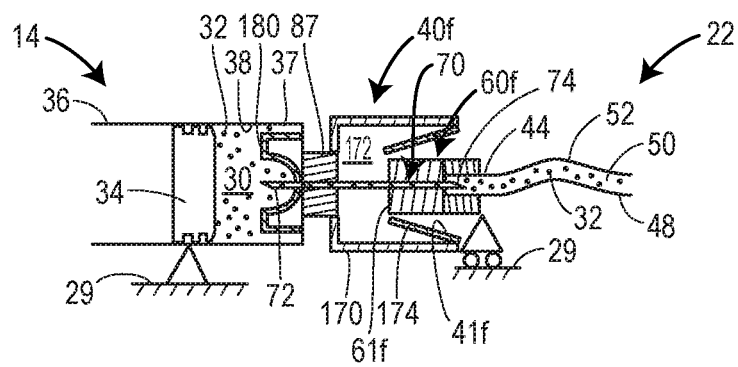

FIGS. 7A-7C depict an embodiment where the second seal member 60f is defined by a pierceable septum similar to the embodiments in FIGS. 5A-6C, and the first seal member 40f is defined by a rigid sleeve 170 defining a sterile interior chamber 172. As shown in FIG. 7A, the sharpened end 74 of the container needle 70 initially may be stored in the sterile interior chamber 172. In some embodiments, the removable membrane 90 may cover an opening at an end of the rigid sleeve 170 opposite to an end of the rigid sleeve 170 attached to the container 14 in order to seal closed the sterile interior chamber 172. In other embodiments, a cover member 174 (e.g., a thin piece of plastic, paper, laminated paper, and/or rubber) positioned between the removable membrane 90 and the rigid sleeve 170 may cover this opening. Unlike the corrugated sleeve 160, the rigid sleeve 170 may not be compressed in length during operation of the drug delivery 10. Instead, the rigid sleeve 170 may be move toward the container 14 (or vice versa) such that the second seal member 60f moves into the sterile interior chamber 172 and is pierced by the sharpened end 74 of the container needle 70 during operation of the drug delivery device 10. The cover member 174 may be deformed or penetrated by the second seal member 60f during this movement so that the second seal member 60f can enter the sterile interior chamber 172. More particularly, as shown in FIG. 7C, during operation of the drug delivery device 10 the distance separating the container 14 and the fluid pathway assembly 22 may be decreased by moving the fluid pathway assembly 22 toward the container 14, or vice versa. As a result, the second seal member 60f may enter the sterile interior chamber 172 of the rigid sleeve 170. The container needle 70 may remain stationary relative to the rigid sleeve 170 during this movement. Consequently, the sharpened end 74 of the container needle 70 may penetrate through the exterior end surface 61f of the second seal member 60f, and then into the fluid passage 50 to establish fluid communication between the reservoir 30 and the fluid passage 50. As illustrated in FIG. 7B, prior to the container needle 70 accessing the fluid passage 50, the membrane removal member 110 or 130 may be actuated to remove the removable membranes 90 and 100 from their respective first and second seal members 40f and 60f, in a manner consistent with the description above.

As illustrated in FIGS. 5A-7C, the embodiments where the container 14 is configured as a syringe may include a deformable reservoir septum 180 disposed within the distal end 37 the reservoir 30. A sterile chamber 182, devoid of the drug 32, may be defined between the deformable reservoir septum 180 and the portion of the wall 38 of the container 14 connected to the container needle 70. Prior to operation of the drug delivery device 10, the first end 72 of the container needle 70, which may be sharpened, may be disposed within the sterile chamber 182 and thus not in fluid communication with the drug 32 in order to prevent leakage of the drug 32 through the container needle 70 prior to operation of the drug delivery device 10. The deformable reservoir septum 180 may be constructed of a fluid impermeable and flexible material, such as rubber, for example, which is capable of being penetrated or pierced by the sharpened end 72 of the container needle 70. As shown in FIGS. 5A, 6A, and 7A, the deformable reservoir septum 180 initially may have a convex configuration, where the sharpened end 72 of the container needle 70 is spaced apart from the deformable reservoir septum. Subsequently, during operation of the drug delivery device 10, the deformable reservoir septum 180 may assume a concave configuration, as shown in FIGS. 5C, 6C, and 7C, where the point of the sharpened end 72 the container needle 70 pierces the deformable reservoir septum 180 to establish fluid communication with the drug 32 in the reservoir 30. The transformation of the deformable reservoir septum 180 from the convex configuration to the concave configuration may be caused by hydraulic pressure resulting from the drive mechanism 24 moving the stopper 34 from the proximal end 36 of the reservoir 30 toward the distal end 37 of the reservoir 30. In other embodiments, the deformable reservoir septum 180 may be omitted such that the first end 72 of the container needle 70 is in fluid communication with the drug 32 in the reservoir 30 prior to and during movement of the stopper 34.

Figure 10A:
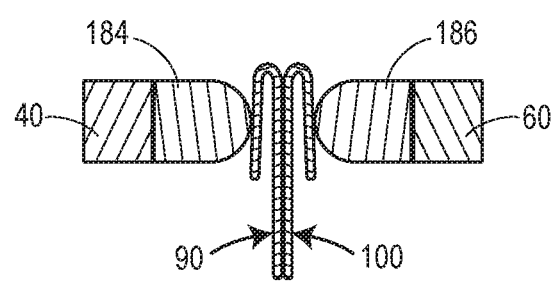
FIGS. 10A and 10B illustrate a schematic cross-sectional view of an embodiment of elastic extension members according to the present disclosure.
Figure 10B:
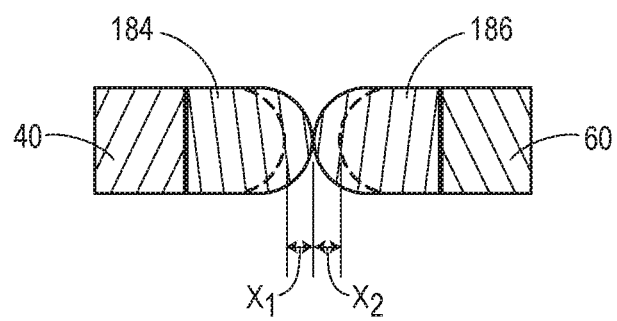

Referring now to FIGS. 10A and 10B, illustrated is an embodiment of a first elastic extension member 184 for extending the length of the first seal member 40 upon removal of the removable membrane 90, and a second elastic extension member 186 for extending the length of the second seal member 60 upon removal of the removable membrane 100. This extension in length may ensure that sterile surfaces are pressed firmly against each other immediately upon removal of the removable membranes 90 and 100. This may reduce the possibility of the ingress of contaminants between the first and second seal members 40 and 60 in the time period between removal of the removable membranes 90 and 100 and the establishment of the fluid flow path between the first and second seal members 40 and 60 via the container needle 70 or the container access needle 80. Accordingly, it may be possible to remove the removable membranes 90 and 100 during assembly of the drug delivery device 10, for example, following installation of the container 14 and the fluid pathway assembly 22 but prior to closure of the housing 29, without risking contamination of the exterior end surfaces 41 and 61 of, respectively, the first and second seal members 40 and 60. This may eliminate the need to include membrane removal member 110 or 130. The first elastic extension member 184 and/or the second elastic extension member 186 may be used in conjunction with any of the embodiments of the first and second seal members 40a-e and 60a-e described above, where appropriate.

As shown in FIG. 10A, initially the first elastic extension member 184 may have an end covering the exterior end surface 41 of the first seal member 40 and a terminal end having a convex configuration. Similarly, initially the second elastic extension member 186 may have an end covering the exterior end surface 61 of the first seal member 60 and a terminal end having a convex configuration. Here, the removable membrane 90 may be adhered to and cover the terminal end of the first elastic extension member 184, and the removable membrane 100 may be adhered to and cover the terminal end of the second elastic extension member 186. As such, the first and second elastic extension members 184 and 186 initially may be spaced apart from each other by the removable membranes 90 and 100 which are positioned between the first and second elastic extension members 184 and 186. Also, in this initial configuration, and via the removable membranes 90 and 100, the first elastic extension member 184 may exert a compressive force against the second elastic extension member 186 and/or the second elastic extension member 186 may exert a compressive force against the first elastic extension member 186. For illustration purposes, FIG. 10a depicts a small gap between the folded ends of the first removable membrane 90 and another small gap between the folded ends of the second removable membrane 100. However, in reality, these gaps would not exist, because the first and second removable membranes 90 and 100 would be compressed tightly between the first elastic extension member 184 and the second elastic extension member 186. In some embodiments, due to the compression between them, opposing ends of the first and second elastic extension members 184 and 186 may have a more flattened contour than that illustrated in FIG. 10a. Following removal of the removable membranes 90 and 100 from the first and second elastic extension members 184 and 186, the first elastic extension member 184 and/or the second elastic extension member 186 may extend in length in direction toward the other one of the first elastic extension member 184 or the second elastic extension member 186, thereby filling the space previously occupied by the removable membranes 90 and 100. The temporary gap created by removal of the removable membranes 90 and 100 may reduce the compressive force between the first and second elastic extension members 184 and 186. With less compressive force present, the first elastic extension member 184 and/or the second elastic extension member 186 may extend in length by a distance X1 or X2 (see FIG. 10B) as a result of their inherent elasticity. Stated another way, the length of each of the first and second elastic extension members 184 and 186 may depend on an amount of compressive force exerted against, respectively, the first and second elastic extension members 184 and 186. The extension in length of the first elastic extension member 184 and/or the second elastic extension member 186 may be caused by the first elastic extension member 184 and/or the second elastic extension member 186 elastically regaining, partially or entirely, their respective original shapes. As a result of this extension in length, the first elastic extension member 184 and the second elastic extension member 186 may directly contact each other with no gap therebetween, as shown in FIG. 10B. In some embodiments, in their respective extended configurations shown in FIG. 10B, the first and second elastic extension members 184 and 186 may exert a compressive force directly against each other, in which case the first elastic extension member 184 and/or the second elastic extension member 186 may only partially elastically regain its respective original shape. The direct contact and/or compressive force between the first and second elastic extension members 184 and 186 in the extended configuration may prevent the ingress of contaminants therebetween. In some embodiments, the first and second elastic extension members 184 and 186 each may be made of material such as rubber, for example, that is capable being pierced by the container needle 70 or the container access needle 80. In some embodiments, only one of the first elastic extension member 184 and the second elastic member 186 may be included, or neither may be included. Furthermore, in some embodiments, the first elastic extension member 184 may be integrally formed with the first seal member 40 such that they form a single component, and/or the second elastic extension member 186 may be integrally formed with the second seal member 60 such that they form a single component.

Methods of assembling the drug delivery device 10 will now be described. Initially, the empty reservoir 30, the first seal member 40, and the removable membrane 90 may be assembled together and sterilized. Next, these components may be aseptically transferred to a filling and capping environment. Here, the reservoir 30 of the container 14 may be filled with the drug 32, and then the proximal and distal ends 36 and 37 of the reservoir 30 may be sealed closed, respectively, with the stopper 34 and the first seal member 40. This filling and capping environment may be operated as a sterile or aseptic assembly environment to ensure that microbes and other contaminants are not captured within the reservoir 30. Subsequently, this drug-filled pre-assembled arrangement may be packaged and shipped to a facility where the final assembly of the drug delivery device 10 is to occur. Also, as a preliminary step, the fluid pathway assembly 22 may be connected to the second seal member 60 such that the second seal member 60 seals closed an open end of the fluid passage 50. Previous to or subsequent to this step, the removable membrane 100 may be adhered or otherwise connected to the exterior end surface 61 of the second seal member 60. The process of assembling the fluid pathway assembly 22, the second seal member 60, and/or the removable membrane 100 may be performed in a Clean Room assembly environment to ensure that particulate contaminants are not captured within the fluid passage 50. Alternatively or additionally, the pre-assembled arrangement of the fluid pathway assembly 22, the second seal member 60, and the removable membrane 100 may be subjected to high-energy sterilization beams (e.g., x-ray radiation beams), ethylene oxide, or other known techniques to ensure their sterility. This pre-assembled arrangement may then be packaged and shipped to a facility where the final assembly of the drug delivery device 10 is to occur.

Subsequently, the drug-filled pre-assembled arrangement of the drug container 14, first seal member 40, and removable membrane 90 and the pre-assembled arrangement of the fluid pathway assembly 22, the second seal member 60, and the removable membrane 100 may be installed within the housing 29 of the drug delivery device 10. Advantageously, this installation process may be carried out in a non-sterile or non-aseptic assembly environment, due to the fact that the exterior end surfaces 41 and 61 of the seal members 40 and 60 are protected from contamination by the removable membranes 90 and 100. In some embodiments, this installation process may involve: connecting the drug-filled pre-assembled arrangement of the container 14, the first seal member 40, and the removable membrane 90 to a first housing portion (e.g., the bottom wall 25 of the housing 29) or a second housing portion (e.g., the top wall 27 of the housing 29) of the drug delivery device 10; and connecting the pre-assembled arrangement of the fluid pathway assembly 22, the second seal member 60, and the removable membrane 100 to the first housing portion or the second housing portion of the drug delivery device 10. Subsequently, the first housing portion may be connected to the second housing portion to enclose the pre-assembled arrangements within the drug delivery device 10. The connection between the first and second housing portions may seal the interior of the drug delivery 10; although a robust seal may not be required because of the protection provided removable seals 90 and 100.

In embodiments including the elastic extension members 184 and 186 depicted in FIGS. 10A and 10B, the method of assembling the drug delivery device 10 may include removing the removable membranes 90 and 100 from their respective seal members 40 and 60 after installation of the drug-filled pre-assembled arrangement of the container 14, first seal member 40, and removable membrane 90 and the pre-assembled arrangement of the fluid pathway assembly 22, second seal member 60, and removable membrane 100 in the first or second housing portion but prior to connecting the first and second housing portions to seal the interior of the drug delivery 10. In such embodiments, the final assembled device 10 may not include the removable membranes 90 and 100 nor the membrane removal member 110 or 130.

Furthermore, in some embodiments, the pre-assembled arrangement of the fluid pathway assembly 22, the second seal member 60, and the removable membrane 100 may be installed in the drug delivery device 10 prior to installation of the drug-filled pre-assembled arrangement of the container 14, the first seal member 40, and the removable membrane 90. In such embodiments, prior to installation of the drug-filled pre-assembled arrangement of the container 14, the first seal member 40, and the removable membrane 90, the pre-assembled arrangement of the fluid pathway assembly 22, the second seal member 60, and the removable membrane 100 may be subjected to high-energy sterilization beams (e.g., x-ray radiation beams), ethylene oxide, and/or any other suitable sterilization technique(s) while it is disposed in the drug delivery device 10. Subsequently, the drug-filled pre-assembled arrangement of the container 14, the second seal member 40, and the removable membrane 90 may be installed in the drug delivery device 10. Thereafter, the drug delivery device 10 may not be subjected to sterilization to avoid damaging the drug 32 within the container 14.

From the foregoing, it can be seen that the present disclosure advantageously provides drug delivery devices, as well as methods for assembly of such devices, that enable a sterile fluid flow path to be established between a drug container and a fluid pathway assembly during operation of the drug delivery device. Furthermore, the removable membranes of the present disclosure advantageously reduce the cleanliness requirements associated with the assembly environment in which the drug container and the fluid pathway assembly may be installed with other components of the drug delivery device. Accordingly, there may not be a need to operate this assembly environment as a sterile or aseptic clean room, which can result in cost and/or time savings. Other benefits and advantages of the present disclosure are apparent from a review of the present disclosure.

Drug Information

As mentioned above, the container of the drug delivery device may be filled with a drug. This drug may be any one or combination of the drugs listed below, with the caveat that the following list should neither be considered to be all inclusive nor limiting.

For example, the syringe may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the syringe may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT, 2xCon4 (N) 1K; L1C; L1C1K; 2xL1C; Con4C; Con4C1K; 2xCon4C1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; Ab1A1; Ab1F; Ab1K, Ab1P; and Ab1P, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present disclosure are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (K), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-05 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgrastim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-B. anthracis protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-C. difficile Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxinl mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-W10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. Nos. 8,030,547, 8,563,698, 8,829,165, 8,859,741, 8,871,913, 8,871,914, 8,883,983, 8,889,834, 8,981,064, 9,056,915, 8,168,762, 9,045,547, 8,030,457, 8,030,457, 8,829,165, 8,981,064, 8,030,457, U.S. Publication No. 2013/0064825, U.S. Patent Application Publication No. 2012/0093818, U.S. Patent Application Publication No. 2013/0079502, U.S. Patent Application Publication No. 2014/0357850, U.S. Patent Application Publication No. 2011/0027287, U.S. Patent Application Publication No. 2014/0357851, U.S. Patent Application Publication No. 2014/0357854, U.S. Patent Application Publication No. 2015/0031870, U.S. Patent Application Publication No. 2013/0085265, U.S. Patent Application Publication No. 2013/0079501, U.S. Patent Application Publication No. 2012/0213797, U.S. Patent Application Publication No. 2012/0251544, U.S. Patent Application Publication No. 2013/0072665, U.S. Patent Application Publication No. 2013/0058944, U.S. Patent Application Publication No. 2013/0052201, U.S. Patent Application Publication No. 2012/0027765, U.S. Patent Application Publication No. 2015/0087819, U.S. Patent Application Publication No. 2011/0117011, U.S. Patent Application Publication No. 2015/0004174, U.S. Provisional Patent Application No. 60/957,668, U.S. Provisional Patent Application No. 61/008,965, U.S. Provisional Patent Application No. 61/010,630, U.S. Provisional Patent Application No. 61/086,133, U.S. Provisional Patent Application No. 61/125,304, U.S. Provisional Patent Application No. 61/798,970, U.S. Provisional Patent Application No. 61/841,039, U.S. Provisional Patent Application No. 62/002,623, U.S. Provisional Patent Application No. 62/024,399, U.S. Provisional Patent Application No. 62/019,729, U.S. Provisional Patent Application No. 62/067,637, U.S. patent application Ser. No. 14/777,371, International Patent Application No. PCT/US2013/048714, International Patent Application No. PCT/US2015/040211, International Patent Application No. PCT/US2015/056972, International Patent Application Publication No. WO/2008/057457, International Patent Application Publication No. WO/2008/057458, International Patent Application Publication No. WO/2008/057459, International Patent Application Publication No. WO/2008/063382, International Patent Application Publication No. WO/2008/133647, International Patent Application Publication No. WO/2009/100297, International Patent Application Publication No. WO/2009/100318, International Patent Application Publication No. WO/2011/037791, International Patent Application Publication No. WO/2011/053759, International Patent Application Publication No. WO/2011/053783, International Patent Application Publication No. WO/2008/125623, International Patent Application Publication No. WO/2011/072263, International Patent Application Publication No. WO/2009/055783, International Patent Application Publication No. WO/2012/0544438, International Patent Application Publication No. WO/2010/029513, International Patent Application Publication No. WO/2011/111007, International Patent Application Publication No. WO/2010/077854, International Patent Application Publication No. WO/2012/088313, International Patent Application Publication No. WO/2012/101251, International Patent Application Publication No. WO/2012/101252, International Patent Application Publication No. WO/2012/101253, International Patent Application Publication No. WO/2012/109530, and International Patent Application Publication No. WO/2001/031007, International Patent Application Publication No. WO/2009/026558, International Patent Application Publication No. WO/2009/131740, International Patent Application Publication No. WO/2013/166448, and International Patent Application Publication No. WO/2014/150983.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, a bispecific T cell engager antibody (BiTe), e.g. Blinotumomab can be used in the device. Alternatively, included can be an APJ large molecule agonist e.g., apelin or analogues thereof in the device. Information relating to such molecules can be found in PCT Publication No. WO 2014/099984.

In certain embodiments, the drug comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the drug comprises a therapeutically effective amount of the anti-TSLP antibody designated as A5 within U.S. Pat. No. 7,982,016.

While the present disclosure has been described in connection with various embodiments, it will be understood that the present disclosure is capable of further modifications. The present disclosure is intended to cover any variations, uses, or adaptations of the disclosed subject matter following, in general, the principles of the present disclosure, and including such departures from the present disclosure as, within the known and customary practice within the art to which the present disclosure pertains.

It is noted that the construction and arrangement of the drug delivery device as shown in the various exemplary embodiments is illustrative only. Although only a few embodiments of the subject matter at issue have been described in detail in the present disclosure, those skilled in the art who review the present disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed herein. For example, elements shown as integrally formed may be constructed of multiple parts or elements, and vice versa. Also, the position of elements may be reversed or otherwise varied, and the nature or number of discrete elements or positions may be altered or varied. Accordingly, all such modifications are intended to be included within the scope of the present disclosure as defined in the appended claims. Furthermore, the order or sequence of any process or method steps may be varied or re-sequenced according to alternative embodiments. Other substitutions, modifications, changes and omissions may be made in the design, operating conditions and arrangement of the various exemplary embodiments without departing from the scope of the present disclosure.

What is claimed is:

1. A drug delivery device comprising:
a housing defining an interior space;
a container disposed in the interior space and including a reservoir containing a drug and a stopper, the stopper being movable through the reservoir from a proximal end of the reservoir toward a distal end of the reservoir to expel the drug from the reservoir during operation of the drug delivery device;
a first seal member connected to the container at the distal end of the reservoir;
a first removable membrane disposed at least partially within the housing and covering an exterior surface of the first seal member to maintain sterility of the exterior surface of the first seal member prior to operation of the drug delivery device;
a fluid pathway assembly configured to establish fluid communication with the reservoir during operation of the drug delivery device and having a first end, a second end, and a fluid passage extending between the first end and the second end;
a second seal member connected to the first end of the fluid pathway assembly; and
a second removable membrane disposed at least partially within the housing and covering an exterior surface of the second seal member to maintain sterility of the exterior surface of the second seal member prior to operation of the drug delivery device.

2. The drug delivery device of claim 1, wherein the first removable membrane and the second removable membrane are positioned immediately adjacent to each other without contacting each other or in direct contact with each other prior to operation of the drug delivery device.

3. The drug delivery device of claim 1, the first removable membrane has a first folded configuration permitting the first removable membrane to unroll when the first removable membrane is pulled away from the first seal member, and the second removable membrane has a second folded configuration permitting the second removable membrane to unroll when the second removable membrane is pulled away from the second seal member.

4. The drug delivery device of claim 1, comprising a container access needle fixed relative to the fluid pathway assembly and having a first end and a second end, the second end being in fluid communication with the fluid passage of the fluid pathway assembly.

5. The drug delivery device of claim 4, the second seal member including a deformable septum having an initial configuration, where the first end of the container access needle is disposed within the deformable septum, and a compressed configuration, where the first end of the container access needle extends outwardly from the deformable septum to pierce the first seal member and thereby establish fluid communication between the reservoir and the fluid pathway assembly.

6. The drug delivery device of claim 5, the deformable septum being at least partially constructed of a first material, wherein a point of the first end of the container access needle is embedded within the first material in the initial configuration.

7. The drug delivery device of claim 6, the second end of the container access needle being rigidly connected to the fluid pathway assembly via a mounting member made of a second material, wherein the second material is more rigid than the first material.

8. The drug delivery device of claim 5, the deformable septum including a corrugated sleeve defining a sterile interior chamber, wherein the first end of the container access needle is disposed within the sterile interior chamber in the initial configuration.

9. The drug delivery device of claim 4, the second seal member including a rigid sleeve defining a sterile interior chamber, wherein the first end of the container access needle is disposed within the sterile interior chamber.

10. The drug delivery device of claim 9, the first seal member or the second seal member being movable relative to the housing between an initial position, where the first seal member is exterior to the rigid sleeve, and an operational position, where the first seal member is at least partially disposed within the rigid sleeve and pierced by a point of the first end of the container access needle to establish fluid communication between the reservoir and the fluid pathway assembly.

11. The drug delivery device of 1, comprising a container needle, the first seal member including a rigid sleeve defining a sterile interior chamber, wherein at least a portion of the container needle is disposed within the sterile interior chamber.

12. The drug delivery device of 16, the first seal member or the second seal member being movable relative to the housing between an initial position, where the second seal member is exterior to the rigid sleeve, and an operational position, where the second seal member is at least partially disposed within the rigid sleeve and pierced by the container needle to establish fluid communication between the reservoir and the fluid pathway assembly.

13. The drug delivery device of claim 1 wherein the exterior surface of the first seal member contacts the exterior surface of the second seal member after the first and second removable membranes are removed from, respectively, the first and second seal members.

14. The drug delivery device of claim 13, comprising a membrane removal member including an adhesive liner covering an exterior surface of the housing, the adhesive liner being pulled away from the housing by a user to expose a skin adhesive disposed on the exterior surface of the housing.

15. An arrangement for a drug delivery device, the arrangement comprising:
   a fluid pathway assembly including
      a first end,
      a second end connectable to an interior element of the drug delivery device,
      a fluid passage extending between the first end and the second end, and
      a seal member connected to the first end of the fluid pathway assembly;
   a container access needle having a first end and a second end, the second end being in fluid communication with the fluid passage and rigidly coupled with the first end of the fluid pathway assembly such that the second end of the container access needle does not move relative to the first end of the fluid pathway assembly during operation of the drug delivery device; and
   a removable membrane covering an exterior surface of the seal member to maintain sterility of the exterior surface of the seal member prior to operation of the drug delivery device.

16. The arrangement of claim 15, the removable membrane having a folded configuration permitting the removable membrane to unroll when the removable membrane is pulled away from the seal member.

17. The arrangement of claim 15, the seal member including a deformable septum having an initial configuration, where the first end of the container access needle is disposed within the deformable septum, and a compressed configuration, where the first end of the container access needle extends outwardly from the deformable septum.

18. The arrangement of claim 15, the seal member including a rigid sleeve defining a sterile interior chamber, wherein the first end of the container access needle is disposed within the sterile interior chamber.

19. A method of assembling a drug delivery device, the method comprising:
   providing a first housing portion and a second housing portion;
   connecting a first pre-assembled arrangement to the first housing portion or the second housing portion, the first pre-assembled arrangement including
      a container having a reservoir containing a drug and a stopper, the stopper being movable through the reservoir from a proximal end of the reservoir toward a distal end of the reservoir to expel the drug from the reservoir during operation of the drug delivery device,
      a first seal member connected to the container at the distal end of the reservoir, and
      a first removable membrane covering an exterior surface of the first seal member to maintain sterility of the exterior surface of the first seal member prior to operation of the drug delivery device, the first removable membrane being disposed at least partially within the first housing portion or the second housing portion as a result of the first pre-assembled arrangement being connected to the first housing portion or the second housing portion; and
   connecting a second pre-assembled arrangement to the first housing portion or the second housing portion under non-sterile or non-aseptic conditions, the second pre-assembled arrangement including
      a fluid pathway assembly having a first end, a second end, and a fluid passage extending between the first end and the second end,
      a second seal member connected to the first end of the fluid pathway assembly, and
      a second removable membrane covering an exterior surface of the second seal member to maintain sterility of the exterior surface of the second seal member prior to operation of the drug delivery device, the second removable membrane being disposed at least partially within the first housing portion or the second housing portion as a result of the second pre-assembled arrangement being connected to the first housing portion or the second housing portion.

20. The method of claim 19, wherein the second pre-assembled arrangement is connected to the first housing portion or the second housing portion prior to connecting the first pre-assembled arrangement to the first housing portion or the second housing portion.

21. The method of claim 20, comprising subjecting the second pre-assembled arrangement to sterilization after connecting the second pre-assembled arrangement to the first housing portion or the second housing portion and before connecting the first pre-assembled arrangement to the first housing portion or the second housing portion.

* * * * *

UNITED STATES PATENT AND TRADEMARK OFFICE
CERTIFICATE OF CORRECTION

PATENT NO. : 11,752,258 B2  
APPLICATION NO. : 16/485407  
DATED : September 12, 2023  
INVENTOR(S) : Yasaman Damestani et al.

Page 1 of 1

It is certified that error appears in the above-identified patent and that said Letters Patent is hereby corrected as shown below:

In the Claims

At Column 34, Line 47, "device of 1," should be -- device of claim 1, --.

At Column 34, Line 52, "device of 16," should be -- device of claim 16, --.

Signed and Sealed this  
Eighth Day of October, 2024

Katherine Kelly Vidal  
*Director of the United States Patent and Trademark Office*